(12) United States Patent
Ellison

(10) Patent No.: US 11,975,051 B1
(45) Date of Patent: May 7, 2024

(54) THERAPEUTIC PEPTIDES AND USES THEREOF

(71) Applicant: Siobhan Ellison, Fairfield, FL (US)

(72) Inventor: Siobhan Ellison, Fairfield, FL (US)

( * ) Notice: Subject to any disclaimer, the term of this patent is extended or adjusted under 35 U.S.C. 154(b) by 33 days.

(21) Appl. No.: 17/811,917

(22) Filed: Jul. 12, 2022

(51) Int. Cl.
| | |
|---|---|
| A61K 38/32 | (2006.01) |
| A61P 13/12 | (2006.01) |
| A61P 25/16 | (2006.01) |
| A61P 25/28 | (2006.01) |
| A61P 29/00 | (2006.01) |

(52) U.S. Cl.
CPC .............. *A61K 38/32* (2013.01); *A61P 13/12* (2018.01); *A61P 25/16* (2018.01); *A61P 25/28* (2018.01); *A61P 29/00* (2018.01)

(58) Field of Classification Search
CPC .......... A61K 38/32; A61P 13/12; A61P 25/16; A61P 29/00; A61P 25/28
See application file for complete search history.

(56) References Cited

U.S. PATENT DOCUMENTS

| | | | |
|---|---|---|---|
| 5,013,723 A | 5/1991 | Sisto et al. | |
| 5,218,089 A | 6/1993 | Mariotti et al. | |

OTHER PUBLICATIONS

Abdelhak et al., *Blood GFAP as an emerging biomarker in brain and spinal cord disorders*, 18 Nature Reviews Neurology 158-172 (2022).
Abiko et al., *Synthesis of [Phe(4F)3]thymopoetin II and examination of its immunological effect on the impaired blastogenic response of T-lymphocytes of uremic patients*, 3(1) Bioorganic & Medicinal Chemistry 1369-1375 (1995) (abstract only).
Arneth, Current Protocols in Cytometry 6.28 supplement 51 (2010) (not provided, if the Examiner wishes to review this document, please alert Applicant).
Audhya et al., *Thymopentin: stability considerations and potency by various route of administration*, 4 Suppl 1 Survey of Immunologic Research 17-23 (1985) (abstract only).
Barde, *Trophic factors and neuronal survival*, 2(6) Neuron 1525-1534 (Jun. 1989).
Basch et al., *Induction of T-Cell Differentiation In Vitro by Thymin, a Purified Polypeptide Hormone of the Thymus*, 71(4) PNAS 1474-1478 (1974).
Bhandari et al., *Edavarone: a new hope for deadly amyotrophic lateral sclerosis*, 54(6) Drugs Today 349-360 (2018).
Bräuer et al., *Effects of the immunomodulator diacetyl-splenopentin on antigen-induced arthritis in rabbits*, 35 (1-2) Agents Actions. 96-103 (1992).
Chen et al., *Overexpression of ferroptosis defense enzyme Gpx4 retards motor neuron disease of SOD1G93A mice*, 11:12890 Nature Portfolio Scientific Reports 1-13 (2021).
Cheroni et al., *Accumulation of human SOD1 and ubiquitinated deposits in the spinal cord of SOD1G93A mice during motor neuron disease progression correlates with a decrease of proteasome*, 18(3) Neurobiol Dis. 509-522 (2005).
Chorev et al., *A dozen years of retro-inverso peptidomimetics*, 26 Acc. Chem. Res. 266-273 (1993).
Cieslak et al., *Purinergic implication in amyotrophic lateral sclerosis-from pathological mechanisms to therapeutic perspectives*, 15(1) Purinergic Signaling 1-15 (2019).
Diezel et al., *Induction and augmentation of mitogen-induced immune interferon production in human lymphocytes by a synthetic thymopoietin pentapeptide*, 43(6) Biomed Biochim Acta. K9-K12 (1984) (abstract only).
Doble, *The pharmacology and mechanism of action of riluzole*, 47 (6 Suppl 4) Neurology 233-41 (1996).
Duchateau et al., *Immunomodulation with thymopentin: in vitro studies*, 6(1) Med. Oncol. Tumor Pharmacother. 19-23 (1989).
Duchateau et al., *In vitro influence of thymopentin on proliferative responses and phytohemagglutinin-induced interleukin 2 production in normal human lymphocyte cultures*, 4 Survey of Immunologic Research 116-124 (1985).
Dupuis et al., *Mitochondria in Amyotrophic Lateral Sclerosis: A Trigger and a Target*, 1(6) Neurodegenerative Diseases 245-254 (2004) (abstract only).
Eckl, *Sensing, signaling and surviving mitochondrial stress*, 78(16) Cellular and Molecular Life Sciences 5925-2951 (2021).
Elfgen et al., *Metabolic resistance of the D-peptide RD2 developed for direct elimination of amyloid-62 oligomers*, 9(5715) Scientific Reports 1-13 (2019).
Erhardt et al., *Tolerance Induction in Response to Liver Inflammation*, 28(1) Immunology and Liver Disease Karger (2010) (abstract only).
Fang et al., *Stage at which riluzole treatment prolongs survival in patients with amyotrophic lateral sclerosis: a retrospective analysis of data from a dose-ranging study*, 17(5) The Lancet Neurology 416-422 (2018).
Fields, *Introduction to Peptide Synthesis*, Current Protocols in Protein Science (Feb. 2002).
Friedmann, *Thymopentin: Safety overview*, 4 Survey of Immunologic Research 139-148 (1985).

(Continued)

*Primary Examiner* — Olga N Chernyshev
(74) *Attorney, Agent, or Firm* — Panitch Schwarze Belisario & Nadel LLP; Erin M. Dunston

(57) ABSTRACT

Methods for ameliorating neurodegenerative disorders and methods for ameliorating inflammatory disorders comprising administering to said subject an effective amount of a polypeptide comprising, in order from N-terminus to C-terminus, R-$X_1$-$X_2$-$X_3$-$X_4$-$X_5$-R' wherein: R is optionally 1-5 additional α-amino acids of either L-configuration or D configuration; $X_1$ is any amino acid of either L-configuration or D-configuration; $X_2$ is any amino acid of either L-configuration or D-configuration; $X_3$ is Asp or Glu of either L-configuration or D-configuration; $X_4$ is any amino acid of either L-configuration or D-configuration; $X_5$ is any amino acid of either L-configuration or D-configuration; and R' is optionally 1-5 additional α-amino acids of either L-configuration or D-configuration, with the proviso that at least three of $X_1$, $X_2$, $X_3$, $X_4$, and $X_5$ are of the D-configuration, wherein the N-terminus is optionally modified by acetylation, and wherein the C-terminus is optionally modified by amidation and/or methylation.

22 Claims, 10 Drawing Sheets
Specification includes a Sequence Listing.

(56) References Cited

OTHER PUBLICATIONS

Ge et al., *Salidroside protects mice against CCl4-induced acute liver injury via down-regulating CYP2E1 expression and inhibiting NLRP3 inflammasome activation*, 85 International Immunopharmacology 106662 (2020) (abstract only).
Ghanta et al., *Survey of thymic hormone effects on physical and immunological parameters in C57BL/6Nnia mice of different ages*, 621 Annals of the New York Academy of Sciences 239-255 (1991) (abstract only).
Goldberg et al., *Contrasting effects of thymopentin and splenopentin on the capacity of female mice to reject syngeneic male skin*, 38(1) Transplantation 52-55 (1984) (abstract only).
Goldberg et al., *Effect of the TP5 analogue of thymopoietin on the rejection of male skin aged and thymectomized female mice*, 13 Immunogenetics 201-204 (1981) (abstract only).
Goldman, *Adult neurogenesis: From canaries to the clinic*, 36(2) Journal of Neurobiology 267-286 (1998).
Gong et al., *The Ubiquitin-Proteasome System: Potential Therapeutic Targets for Alzheimer's Disease and Spinal Cord Injury*, 9(Article 4) Frontiers in Molecular Neuroscience 1-16 (2016).
H. Wang et al., *Immune mechanisms of Concanavalin A model of autoimmune hepatitis*, 18(2) World Journal of Gastroenterology 119-125 (2012).
Herdewyn et al., *Prevention of intestinal obstruction reveals progressive neurodegeneration in mutant TDP-43 (A315T) mice*, 9 Molecular Neurodegeneration 24 (2014).
Hill et al., *Role of Signaling Molecules in Mitochondrial Stress Response*, 9(225) Frontiers in Genetics 1-9 (2018).
Homma et al., *Edaravone, a free radical scavenger, protects against ferroptotic cell death in vitro*, 384(1) Exp. Cell. Res. 111592 (2019).
Hor et al., *ALS motor neurons exhibit hallmark metabolic defects that are rescued by SIRT3 activation*, 28 Cell Death & Differentiation 1379-1397 (2021).
Hu et al., *In vivo enhancement of NK-cell activity by thymopentin*, 12(2) International Journal of Immunopharmacology 193-197 (1990) (abstract only).
Kalliolias et al., *TNF biology, pathogenic mechanisms and emerging therapeutic strategies*, 12(1) Nature Reviews Rheumatology 49-62 (2016).
Kaur et al., *A panoramic review of IL-6: Structure, pathophysiological roles and inhibitors*, 28(5) Bioorg. Med. Chem. 115327 (2020).
Komine et al., *Neuroinflammation in motor neuron disease*, 77(4) Nagoya J. Med. Sci. 537-549 (2015).
Lamas et al., *Harnessing the Potential of Human Pluripotent Stem Cell-Derived Motor Neurons for Drug Discovery in Amyotrophic Lateral Sclerosis: From the Clinic to the Laboratory and Back to the Patient*, 1(773424) Frontiers in Drug Discovery 1-26 (2021).
Lau et al., *Functional effects of thymopoietin32-36 (TP5) on cytotoxic lymphocyte precursor units (CLP-U). I. Enhancement of splenic CLP-U in vitro and in vivo after suboptimal antigenic stimulation*, 124(4) J. Immunol 1861-1865 (1980) (abstract only).
Lee et al., *Partial Retro-Inverso, Retro, and Inverso Modifications of Hydrazide Linked Bifunctional Peptides for Opioid and Cholecystokinin (CCK) Receptors*, 50(1) J. Med Chem. 165-168 (2007).
Liu et al., *Peripheral and Central Nervous System Immune Response Crosstalk in Amyotrophic Lateral Sclerosis*, 14(Article 575) Frontiers in Neuroscience 1-16 (2020).
Lutz, *Mouse models of ALS: Past, present and future*, 1693(Pt A) Brain Research 1-10 (2018).
Malchow et al., *Essential role of neutrophil mobilization in concanavalin A-induced hepatitis is based on classic IL-6 signaling but not on IL-6 trans-signaling*, 1812 Biochimica Et Biophysica Acta 290-301 (2011).
Mora et al., *Biodistribution of synthetic thymosin beta 4 in the serum, urine, and major organs of mice*, 19(1) Int. J. Immunopharmacol. 1-8 (1997) (abstract only).

Nicoletti et al., *The Effects of Thymopentin on the Development of SLE-Like Syndrome in the MRL/lpr-lpr Mouse*, 40(5) Scandinavian Journal of Immunology 549-556 (1994).
Ochoa, *Arg-Lys-Asp-Val-Tyr (Thymopentin) Accelerates the Cholinergic-Induced Inactivation (Desensitization) of Reconstituted Nicotinic Receptor*, 8(3) Cellular and Molecular Neurobiology 325-331 (1988).
Post et al., *A Novel Anti-Inflammatory D-Peptide Inhibits Disease Phenotype Progression in an ALS Mouse Model*, 26 Molecules 2-16 (2021).
R. Götz et al., *The conservation of neurotrophic factors during vertebrate evolution*, 108(1) Comp. Biochem Physiol Pharmacol Toxicol Endocrinol. 1-10 (1994).
Scheid et al., *The generation and regulation of lymphocyte populations: evidence from differentiative induction systems in vitro*, 147(6) J. Exp. Med. 1727-1743 (1978).
Severa et al., *Thymosins in multiple sclerosis and its experimental models: moving from basic to clinical application*, 27 Multiple Sclerosis and Related Disorders 52-60 (2019).
Singh et al., *Thymopentin and splenopentin as immunomodulators. Current status*, 17(3) Immunol. Res. 345-368 (1998) (abstract only).
Singh et al., *Neuronal mitochondrial dysfunction in sporadic amyotrophic lateral sclerosis is developmentally regulated*, 11:18916 Nature Scientific Reports 1-16 (2021).
Spasić, *Edaravone May Prevent Ferroptosis in ALS*, 21(8) Curr. Drug Targets 776-780 (2020).
Stephenson et al., *Modeling amyotrophic lateral sclerosis in mice*, 25-26 Drug Discovery Today: Disease Models 35-44 (2017).
Suk et al., *The role of TDP-43 mislocalization in amyotrophic lateral sclerosis*, 15:45 Molecular Neurodegeneration 1-16 (2020).
Sun et al., *Erastin induces apoptotic and ferroptotic cell death by inducing ROS accumulation by causing mitochondrial dysfunction in gastric cancer cell HGC-27*, 22(4) Mol. Med Rep. 2826-2832 (2020).
Sundal et al., *Management of viral infections with thymopentin*, 44(7) Arzneimittel-Forschung 866-871 (1994) (abstract only).
Thomazelli et al., *Concanavalin-A displays leishmanicidal activity by inducing ROS production in human peripheral blood mononuclear cells*, 40(5) Immunopharmacology and Immunotoxicology 387-392 (2018).
Tuthill et al., *Thymosin Alpha 1—A Peptide Immune Modulator with a Broad Range of Clinical Applications*, 3(4) Journal of Clinical and Experimental Pharmacology 1-17 (2013).
Umeda et al., *Frontline Science: Concanavalin A-induced acute hepatitis is attenuated in vitamin D receptor knockout mice with decreased immune cell function*, 106(4) Leukocyte Biology 791-801 (2019).
Vijayan et al., *Structure-based inhibitor screening of natural products against NSP15 of SARS-CoV-2 revealed thymopentin and oleuropein as potent inhibitors*, 12 Journal of Proteins and Proteomics 71-80 (2021).
Volonte et. al., *Purinergic contribution to amyotrophic lateral sclerosis*, 104 Neuropharmacology 180-193 (2016) (abstract only).
Wang et al., *Activation of interferon signaling pathways in spinal cord astrocytes from an ALS mouse model*, 59(6) GLIA 946-958 (2011).
Wang et al., *Ferroptosis mediates selective motor neuron death in amyotrophic lateral sclerosis*, Cell Death Differ, PMID: 34857917 (2021).
Weksler et al., *Immunological studies of aging. IV. The contribution of thymic involution to the immune deficiencies of aging mice and reversal with thympoietin32-36*, 148(4) J. Exp. Med. 996-1006 (1978).
Yao et al., *Thymosin-alpha1 modulates dendritic cell differentiation and functional maturation from human peripheral blood CD14+ monocytes*, 110(2) Immunol Lett. 110-120 (2007).
Yu et al., *Ferroptosis, a new form of cell death, and its relationships with tumorous diseases*, 21(4) Journal of Cellular and Molecular Medicine 648-657 (2017).
Zhang et al., *An APP ectodomain mutation outside of the Aβ domain promotes Aβ production in vitro and deposition in vivo*, 218(6) Journal of Experimental Medicine e20210313 1-20 (2021).

(56) References Cited

OTHER PUBLICATIONS

Zou et al., *The effect of thymopentin on immune function and inflammatory levels in end-stage renal disease patients with maintenance hemodialysis*, 14(1) Am. J. Transl. Res. 414-420 (2022).
Betjes, *Immune cell dysfunction and inflammation in end-stage renal disease*, 9 Nature Reviews 255-265 (May 2013).

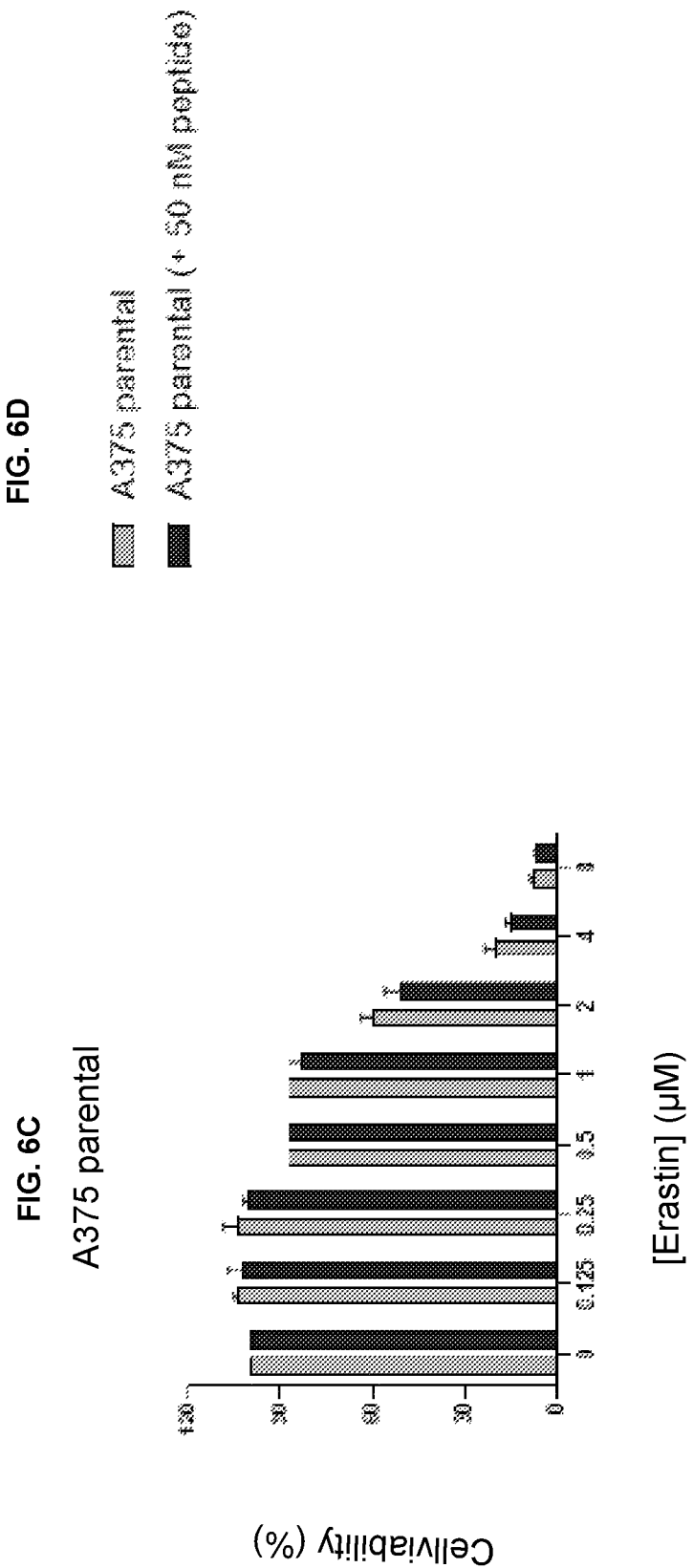

FIG. 7A
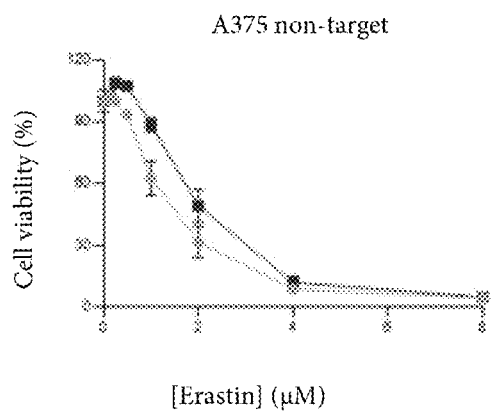
FIG. 7B
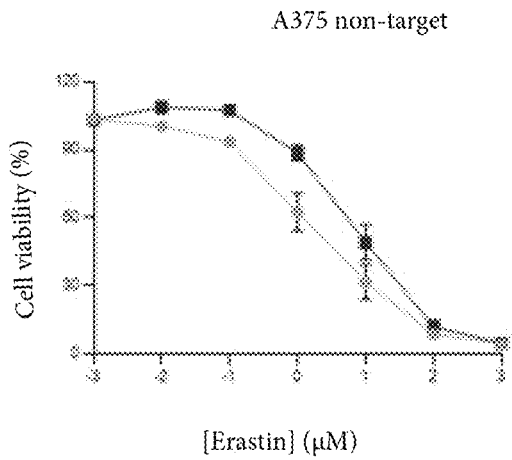
FIG. 7C
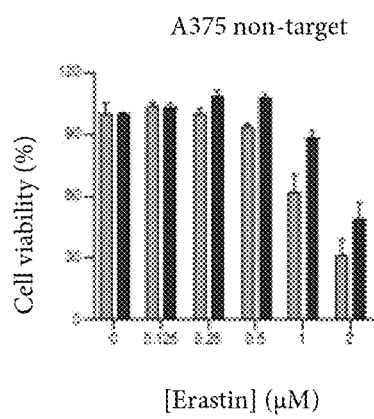
FIG. 7D
▨ A375 non-target
■ A375 non-target (+ 50 nM peptide)

THERAPEUTIC PEPTIDES AND USES THEREOF

REFERENCE TO SEQUENCE LISTING SUBMITTED ELECTRONICALLY

This application contains a Sequence Listing, which has been submitted electronically via EFS-Web as an XML formatted sequence listing with a file name 6898010001_Sequence_Listing, creation date of Sep. 20, 2022, and having a size of 27,451 bytes. The Sequence Listing is part of the specification and is herein incorporated by reference in its entirety.

BACKGROUND OF THE INVENTION

The present invention relates to polypeptide inverse analogs of thymopentin (also known as "TP-5") and the use of those inverse analogs for ameliorating disorders.

Background of Amyotrophic Lateral Sclerosis ("ALS")

ALS is a clinically-heterogeneous disorder characterized by degeneration of upper motor neurons in the brain stem and lower motor neurons in the spinal cord. ALS is prevalent in the United States, with reports of 5.5 cases per 100,000 residents. Multiple mechanisms of motor neuron injury have been implicated, including more than 20 different genetic factors in familial ALS. See M. Cieślak et al., *Purinergic implication in amyotrophic lateral sclerosis—from pathological mechanisms to therapeutic perspectives*, 15(1) PURINERGIC SIGNALING 1-15 (2019). Non-familial ALS is called sporadic ALS ("sALS") and comprises the majority of the cases. The causes of sALS are unknown, yet all ALS cases are considered genetic and sALS patients present without a clear family history.

The pathogenesis of ALS consists of two stages: an early neuroprotective stage and a later neurotoxic stage. During early phases of disease progression, the immune system through microglia and T cell activities provides anti-inflammatory factors that sustain motor neuron viability. As the disease progresses and motor neuron injury accelerates, a rapidly succeeding neurotoxic phase develops. A well-orchestrated purine-mediated dialog among motor neurons, surrounding glia and immune cells control the beneficial and detrimental activities occurring in the nervous system. Given the complex cellular cross-talk occurring in ALS and the recognized function of extracellular nucleotides and adenosine in neuroglia communication, restoring purinome dynamics might provide efficient treatment to slow the progression of disease. See M. Cieślak et al., *Purinergic implication in amyotrophic lateral sclerosis—from pathological mechanism to therapeutic perspectives*, 15(1) PURINERGIC SIGNALING 1-15 (2019); Z. Liu et al., *Peripheral and Central Nervous System Immune Response Crosstalk in Amyotrophic Lateral Sclerosis*, 14(Article 575) FRONTIERS IN NEUROSCIENCE 1-16 (2020); C. Volonte et. al., *Purinergic contribution to amyotrophic lateral sclerosis*, 104 NEUROPHARMACOLOGY 180-193 (2016); T. Singh et. al., *Neuronal mitochondrial dysfunction in sporadic amyotrophic lateral sclerosis is developmentally regulated*, 11:18916 NATURE SCIENTIFIC REPORTS 1-16 (2021).

ALS is a final common denominator for many kinds of environmental and genetic (ecogenic) problems. No single person will have the same triggers, but everyone comes down with the same disease, ALS, because disease is a conserved way that the body reacts to many kinds of problems.

There are many cataloged, strong, single-gene causes and more strong environmental links to ALS. No ALS patient has all the possible causes. And no single genetic or environmental cause accounts for more than a few cases. This makes ALS a "pluricausal" disease. Because ALS is like so many chronic diseases it progresses down a final common response. The basis for mechanisms driving healing may be mitochondria and ATP, purinergic, signaling. In view of this, drugs that inhibit inflammatory signaling caused by extracellular ATP ("eATP") will be pluribeneficial because they target the common response, not a common cause (that does not exist).

Only two FDA-approved treatments are available for ALS patients, Riluzole and Edavarone, but both have marginal effects slowing the progression of disease. Riluzole is a neuroprotective drug that blocks glutamatergic neurotransmission in the CNS (see A. Doble, *The pharmacology and mechanism of action of riluzole*, 47 (6 Suppl 4) NEUROLOGY 233-41 (1996)) and is associated with a prolonged stage 4 disease, not prolonging stages 2 or 3 or generally slowing disease in patients with ALS. See T. Fang et. al., *Stage at which riluzole treatment prolongs survival in patients with amyotrophic lateral sclerosis: a retrospective analysis of data from a dose-ranging study*, 17(5) THE LANCET NEUROLOGY 416-422 (2018). Riluzole may extend life by several months. Edavarone is an antioxidant that prevents oxidative stress from inducing motor neuron death and slows the progression of disease by 33% in ALS patients. See R. Bhandari et al., *Edavarone: a new hope for deadly amyotrophic lateral sclerosis*, 54(6) DRUGS TODAY 349-360 (2018).

Despite many promising compounds identified in preclinical studies in the $SOD1^{G93A}$ murine model, the most accepted ALS model drug effectiveness testing, few drugs have translated to clinical effectiveness in people. See J. Stephenson et al., *Modeling amyotrophic lateral sclerosis in mice*, 25-26 DRUG DISCOVERY TODAY: DISEASE MODELS 35-44 (2017). It is generally accepted that using mouse models to investigate an aspect of ALS and using a wider range of ALS mouse models in drug development would be beneficial for drug discovery, however the models of murine ALS are significantly different than human ALS. That is to say, no single model can reflect the full spectrum of ALS, many current mouse models can emulate specific disease facets. See C. Lutz, *Mouse models of ALS: Past, present and future*, 1693(Pt A) BRAIN RESEARCH 1-10 (2018).

In vitro cell assays are valuable, non-invasive, and available tools to investigate purinergic mediated signaling in a patient or group of patients. The source of the cells are important and include induced pluripotent stem cells and endothelial cells from sources such as adipose or skin cells.

There is an urgent need to find tools for drug discovery that could impact on the course of ALS, with the ultimate goal to extend the life of patients and improve their quality of life. Induced pluripotent stem cells ("iPSCs"), similarly to embryonic stem cells ("ESCs"), have the capacity to differentiate into all three embryonic germ layers, which offers the unprecedented opportunity to access patient-specific central nervous system cells in an inexhaustible manner. Human MNs generated from ALS patient iPSCs are tools for disease modelling and drug discovery projects, they display ALS-specific phenotypes. See N.J. Lamas et al., *Harnessing the Potential of Human Pluripotent Stem Cell-Derived Motor Neurons for Drug Discovery in Amyotrophic Lateral Sclerosis: From the Clinic to the Laboratory and Back to the Patient*, 1(773424) FRONTIERS IN DRUG DISCOVERY 1-26 (2021). The differentiated iPSCs revert to the embryonic stage of the patient. Overcoming this issue, it is possible to use endothelial cells that reflect the cellular chronicity of the patient.

While there is no single trigger to a pluricausal disease there is a common pathway to healing and recovery. Purinergic signaling normalizes a dysregulated eATP pathway and slows the progress of ALS.

Thymic Hormones

Thymic hormones are intricately involved with immunologic differentiation and regulation. Regulatory peptides derived from thymopoietin induce cytokine subsets with varied outcomes in metabolic and immune pathways that are important in homeostasis and disease processes. See T. K. Audhya et al., *Thymopentin: stability considerations and potency by various route of administration*, 4 Suppl 1 SURVEY OF IMMUNOLOGIC RESEARCH 17-23 (1985). Mitochondrial dysfunction is a prevalent feature of many neurodegenerative diseases, including motor neuron disorders such as ALS. Mitochondria play a central role in excitotoxicity, oxidative stress, and apoptosis but the link between pathology and mitochondrial stress is unknown.

Neurotrophic factors are endogenous proteins that modulate cell signaling pathways regulating stem cell proliferation, neuronal differentiation, cell growth, and regeneration. See Y. A. Barde, *Trophic factors and neuronal survival*, 2(6) NEURON 1525-1534 (1989); R. Götz et al., *The conservation of neurotrophic factors during vertebrate evolution*, 108(1) COMP. BIOCHEM PHYSIOL PHARMACOL TOXICOL ENDOCRINOL. 1-10 (1994); S. Goldman, *Adult neurogenesis: From canaries to the clinic*, 36(2) JOURNAL OF NEUROBIOLOGY 267-286 (1998). They are generally small, soluble proteins with molecular weights under 24 kilodaltons ("Kda"). Because of their physiological role, neurotrophic factors are useful in treating the degeneration of nerve cells and the loss of differentiated function that occurs in a variety of neurodegenerative diseases. Identifying neurotrophic factors with a combination of protective and restorative actions on multiple pathological pathways and developing effective strategies for drug delivery have profound therapeutic implications for ALS and other degenerative processes in the central nervous system ("CNS").

Thymopentin ("TP-5," whose synonyms include immunox, sintomodulina, thymopoietin 32-26, thymopoietin pentapeptide, thymopoietin pentapeptide-fluorescin-isothicyanate, N~5~-(diaminomethylidene)ornithyllysyl-alpha-aspartylvalyltyrosine, and N~5~-(diaminomethylidene)-L-ornithyl-L-lysyl-L-alpha-aspartyl-L-valyl-L-tyrosine, with a CAS number of 69558-55-0 and a molecular mass of 679.765) is the synthetic pentapeptide Arg-Lys-Asp-Val-Tyr (SEQ ID NO:6) corresponding to amino acid residues 32-36 of the thymic hormone thymopoietin. Thymopentin is the minimal sequence that reproduces the biological activities of thymopoietin and is an immunostimulant and anti-inflammatory agent. Products containing thymopentin include TIMUNOX®, Mepentil, and SINTOMODULINA®, which are used for primary immunodeficiencies, secondary immunodeficiencies, in complications of cancer patients after chemotherapy, and for the stimulation of immune responses. Thymopentin is a soluble peptide hormone with pleiotropic effects. Both in vitro and in vivo studies have been conducted to show the multiple roles of thymopentin. See V. K. Singh et al., *Thymopentin and splenopentin as immunomodulators. Current status*, 17(3) IMMUNOL. RES. 345-368 (1998). Thymopentin induced the differentiation of early T cells (thymocytes) from bone marrow or spleen (see R. S. Basch et al., *Induction of T-Cell Differentiation In Vitro by Thymin, a Purified Polypeptide Hormone of the Thymus*, 71(4) PNAS 1474-1478 (1974)); inhibited B cell differentiation (see M. P. Scheid et al., *The generation and regulation of lymphocyte populations: evidence from differentiative induction systems in vitro*, 147(6) J. EXP. MED. 1727-1743 (1978)); and induced lymphocyte proliferation in vitro (see T. Abiko et al., *Synthesis of [Phe(4F)$^3$]thymopoetin II and examination of its immunological effect on the impaired blastogenic response of T-lymphocytes of uremic patients*, 3(1) BIOORGANIC & MEDICINAL CHEMISTRY 1369-1375 (1995)). Thymopentin demonstrated a dose dependent stimulation or inhibition of mitogen-induced IgG, T cell proliferation, and enhanced synthesis of IL-2 in vivo. See J. Duchateau et al., *Immunomodulation with thymopentin: in vitro studies*, 6(1) MED. ONCOL. TUMOR PHARMACOTHER. 19-23 (1989); J. Duchateau et al., *In vitro influence of thymopentin on proliferative responses and phytohemagglutinin-induced interleukin 2 production in normal human lymphocyte cultures*, 4 SURVEY OF IMMUNOLOGIC RESEARCH 116-124 (1985). Additional in vitro mitogen-induced responses include IFN production and enhanced NK cell activity in mice cells. See W. Diezel et al., *Induction and augmentation of mitogen-induced immune interferon production in human lymphocytes by a synthetic thymopoietin pentapeptide*, 43(6) BIOMED BIOCHIM ACTA. K9-K12 (1984); C. Hu et al., *In vivo enhancement of NK-cell activity by thymopentin*, 12(2) INTERNATIONAL JOURNAL OF IMMUNOPHARMACOLOGY 193-197 (1990). Immunomodulatory actions from in vivo studies demonstrated TP5 blocked neurotransmission and restored helper T cell activity (see M. C. Weksler et al., *Immunological studies of aging. IV. The contribution of thymic involution to the immune deficiencies of aging mice and reversal with thympoietin32-36*, 148(4) J. EXP. MED. 996-1006 (1978)), restored tolerance and reduced skin graft rejection (see E. H. Goldberg et al., *Effect of the TP5 analogue of thympoieton on the rejection of male skin aged and thymectomized female mice*, 13 IMMUNOGENETICS 201-204 (1981); E. H. Goldberg et al., *Contrasting effects of thymopentin and splenopentin on the capacity of female mice to reject syngeneic male skin*, 38(1) TRANSPLANTATION 52-55 (1984)), although low doses enhanced cytotoxic lymphocyte activity (see C. Y. Lau et al., *Functional effects of thymopoietin32-36 (TP5) on cytotoxic lymphocyte precursor units (CLP-U). I. Enhancement of splenic CLP-U in vitro and in vivo after suboptimal antigenic stimulation*, 124(4) J. IMMUNOL 1861-1865 (1980)) and short-term treatment did not restore immune function (see V. K. Ghanta et al., *Survey of thymic hormone effects on physical and immunlogical parameters in C57BL/6Nnia mice of different ages*, 621 ANNALS OF THE NEW YORK ACADEMY OF SCIENCES 239-255 (1991)).

Importantly, autoimmunity was affected by administration of TP-5, demonstrated by turning off autoantibody formation (see C. Y. Lau et al., *Functional effects of thymopoietin32-36 (TP5) on cytotoxic lymphocyte precursor units (CLP-U). I. Enhancement of splenic CLP-U in vitro and in vivo after suboptimal antigenic stimulation*, 124(4) J. IMMUNOL 1861-1865 (1980)), inhibiting antigen-induced arthritis in rats (see R. Bräuer et al., *Effects of the immunomodulator diacetyl-splenopentin on antigen-induced arthritis in rabbits*, 35 (1-2) AGENTS ACTIONS. 96-103 (1992)), enhancing OKT4$^+$ cells (see E. Sundal et al., *Management of viral infections with thymopentin*, 44(7) ARZNEIMITTEL-FORSCHUNG 866-871 (1994)) and modulating autoimmunity in systemic lupus erythematosus mouse models (see F. Nicoletti et al., *The Effects of Thymopentin on the Development of SLE-Like Syndrome in the MRL/Ipr-Ipr Mouse*, 40(5) SCANDINAVIAN JOURNAL OF IMMUNOLOGY 549-556 (1994)). Tumors were reduced or prevented and there was a delayed onset of tumor-induced immune suppression with administration of TP5 in some studies (see V. K. Singh et al., *Thymopentin and splenopentin as immunomodulators. Current status*, 17(3) IMMUNOLOGIC RESEARCH 345-368 (1998)). Prevention of radiation damage and improved survival was seen in some studies.

More recently, thymopentin was shown to bind NSP15, a non-structural protein that is expressed by SARS-CoV2. See R. Vijayan et al., *Structure-based inhibitor screening of natural products against NSP15 of SARS-CoV-2 revealed thymopentin and oleuropein as potent inhibitors*, 12 JOURNAL OF PROTEINS AND PROTEOMICS 71-80 (2021). NSP15 is a nidoviral RNA uridylate-specific endoribonuclease of corona virus that interferes with the innate immune response of the host and is important for disease progression and virulence. NSP15 suppresses type 1 IFN-(α/β)-associated innate immune response by infecting the macrophage. In renal dialysis patients thymopentin reduced IL-6, IL-8, TNF, and CRP, indicating that treatment notably reduced the inflammatory responses in the body and inhibit an acute phase response induced by end-stage renal disease. See Q. Zou et al., *The effect of thymopentin on immune function and inflammatory levels in end-stage renal disease patients with maintenance hemodialysis*, 14(1) AM. J. TRANSL. RES. 414-420 (2022). In the same study, thymopentin improved the state of oxidative stress by increasing superoxide dismutase ("SOD"), a major antioxidant enzyme that inhibits the accumulation of lipid peroxides. Id.

ALS and related disorders, such as Alzheimer's disease, Parkinson's disease, frontotemporal lobar degeneration, chronic traumatic encephalopathy, and inclusion body myositis among others, are a spectrum of diseases that may converge on common pathologies that could be treatable by ultimately regulating and slowing disease progression, such as neuroinflammation. Thymic hormones are intricately involved with immunologic differentiation and regulation and may play a role in altering dysregulated pathways in disease. Regulatory peptides derived from thymopoietin induce cytokine subsets with varied outcomes in metabolic and immune pathways that are important in homeostasis and disease processes. Mitochondrial dysfunction is a prevalent feature of many neurodegenerative diseases, including motor neuron disorders such as ALS. Mitochondria play a central role in excitotoxicity, oxidative stress, and apoptosis but the link between pathology and mitochondrial stress is unknown. See, e.g., L. Dupuis et al., *Mitochondria in Amyotrophic Lateral Sclerosis: A Trigger and a Target*, 1(6) NEURODEGENERATIVE DISEASES 245-254 (2004). There is substantial evidence that inflammation is associated with the death of motor neurons in ALS. See O. Komine et al., *Neuroinflammation in motor neuron disease*, 77(4) NAGOYA J. MED. SCI. 537-549 (2015).

Degeneration and death of motor neurons in ALS are associated with increased lipid peroxidation. Lipid peroxidation is the driver of ferroptosis, an iron-dependent oxidative mode of cell death. See L. Chen et al., *Overexpression of ferroptosis defense enzyme Gpx4 retards motor neuron disease of SOD1G93A mice*, 11:12890 NATURE PORTFOLIO SCIENTIFIC REPORTS 1-13 (2021). Increased lipid peroxidation has been reported in ALS patients and ALS mouse models, suggesting that ferroptosis may be involved in the pathogenesis of ALS. Wang et al. confirmed the lack of expression of key necroptotic effector proteins in the spinal cords of ALS patients, they showed depletion of glutathione peroxidase 4 (GPX4), an anti-oxidant enzyme and central repressor of ferroptosis, occurred in post-mortem spinal cords of both sporadic and familial ALS patients. See T. Wang et al., *Ferroptosis mediates selective motor neuron death in amyotrophic lateral sclerosis*, CELL DEATH DIFFER, PMID: 34857917 (2021).

Ferroptosis is a newly-discovered type of cell death that differs from traditional apoptosis and necrosis and results from iron-dependent lipid peroxide accumulation. See H. Yu et al., *Ferroptosis, a new form of cell death, and its relationships with tumourous diseases*, 21(4) JOURNAL OF CELLULAR AND MOLECULAR MEDICINE 648-657 (2017). Ferroptotic cell death is characterized by cytological changes, including cell volume shrinkage and increased mitochondrial membrane density. Ferroptosis can be induced by two classes of small-molecule substances known as class 1 (system $X_c^-$ inhibitors) and class 2 ferroptosis inducers, glutathione peroxidase 4 (GPx4) inhibitors. The free radical scavenger Edavarone is clinically approved for the treatment of ALS and protects against ferroptotic cell death in vitro. See T. Homma et al., *Edaravone, a free radical scavenger, protects against ferroptotic cell death in vitro*, 384(1) EXP. CELL. RES. 111592 (2019); S. Spasić, *Edaravone May Prevent Ferroptosis in ALS*, 21(8) CURR. DRUG TARGETS 776-780 (2020).

Ferroptosis is a nonapoptotic, iron-dependent form of cell death that can be activated in cancer cells by natural stimuli and synthetic agents. Three essential hallmarks define ferroptosis, namely: the loss of lipid peroxide repair capacity by the phospholipid hydroperoxidase GPX4, the availability of redox-active iron, and oxidation of polyunsaturated fatty acid ("PUFA")-containing phospholipids. A novel, non-ferroptotic cell death pathway mediated by type 1 interferon ("type 1 IFN") was proposed by Zhang. See X. Zhang et al., *An APP ectodomain mutation outside of the Aβ domain promotes Aβ production in vitro and deposition in vivo*, 218(6) JOURNAL OF EXPERIMENTAL MEDICINE e20210313 1-20 (2021). Activation of IFN signaling pathways represent an early dialogue between motor neurons and astrocytes in response to pathological changes in ALS. See R. Wang et al., *Activation of interferon signaling pathways in spinal cord astrocytes from an ALS mouse model*, 59(6) GLIA 946-958 (2011).

Erastin induces apoptotic and ferroptotic cell death in some cancer cell lines. See Y Sun et al., *Erastin induces apoptotic and ferroptotic cell death by inducing ROS accumulation by causing mitochondrial dysfunction in gastric cancer cell HGC-27*, 22(4) MOL. MED REP. 2826-2832 (2020). Briefly, cells are cultured and treated and analyzed for cell viability. Drugs that affect ferroptotic cell death can be explored by inhibiting Erastin and monitoring the effects on cells by viability assays.

Thymosins act as a neurotropic factors targeting neurons, oligodendrocytes, and microglia and provide neuroprotection, immunosuppression, and neurorestoration including remyelination, synaptogenesis and axon growth. See M. Severa et al., *Thymosins in multiple sclerosis and its experimental models: moving from basic to clinical application*, 27 MULTIPLE SCLEROSIS RELATED DISORDERS 52-60 (2019). The therapeutic benefits of synthetic thymosins based on the sequence of TP5 were observed in the CNS of some neurological disorders, including multiple sclerosis ("MS"), presumably because it crosses the blood brain barrier after exogenous administration. See C. A. Mora et al., *Biodistribution of synthetic thymosin beta 4 in the serum, urine, and major organs of mice*, 19(1) INT. J. IMMUNOPHARMACOL. 1-8 (1997). In vivo studies demonstrated the effects of thymosin on neuromuscular transmission and the ability to induce T cell differentiation. See E. L. M. Ochoa, *Arg-Lys-Asp-Val-Tyr (Thymopentin) Accelerates the Cholinergic-Induced Inactivation (Desensitization) of Reconstituted Nicotinic*

*Receptor,* 8(3) CELLULAR AND MOLECULAR NEUROBIOLOGY 325-331 (1988). The therapeutic benefit of TP5 may be on one or more mediators of neuroinflammation. Prothymosin α, the precursor of thymosin α ("thymalfasin," or "Tα1"), regulated defective phenotype monocytes in MS, impacting T cell activation. Commercially-available Tα1, ZADAXIN®, is proposed for treatment of chronic hepatitis B, chronic hepatitis C, and as adjunctive cancer therapy as an immunomodulator.

To summarize, both in vitro and in vivo studies have established the multiple roles of thymopentin. The action of TP5 was demonstrated on immune cells from bone marrow or spleen, inhibited B cell differentiation, and normalization of induced lymphocytes demonstrated by a dose-dependent regulation of mitogen-induced IgG, T cell proliferation, and enhanced synthesis of IL-2. Additional in vitro mitogen-induced responses include interferon (IFN) production and enhanced NK cell activity in mouse cells. Immunomodulatory actions from in vivo studies demonstrated TP5 blocked neurotransmission and restored helper T cell activity and restored tolerance and reduced skin graft rejection although low doses enhanced cytotoxic lymphocyte activity and short-term treatment did not restore immune function.

Autoimmunity was affected by administration of TP5, demonstrated by turning off autoantibody formation, inhibiting antigen-induced arthritis in rats, enhancing OKT4$^+$ cells and modulating autoimmunity in systemic lupus erythematosus mouse models. Some tumors were reduced or prevented and there was a delayed onset of tumor-induced immune suppression with administration of TP5 in some studies for breast cancer, head and neck tumors, and carcinomas but no benefits in renal cancers. Prevention of radiation damage and improved survival was seen in some studies. Based on the prolific in vitro studies clinical studies were conducted for various cancers, immunodeficiencies, atopic dermatitis, autoimmunity, infections, and other maladies.

ZADAXIN® (pro-Tα1) is used to augment T cell function, promote T cell differentiation and maturation, and increase IFNγ, IFNα, IL-2, IL-3 and Il-2r following mitogen activation, increase NK cell activity, increase migratory inhibitory factor ("MIF"), and increase antibody response to T cell dependent antigens. The mechanism of action of Tα1 on the immune system is unknown, however signaling via p38 MAPK and NFκB are proposed. See Q. Yao et al., *Thymosin-alpha1 modulates dendritic cell differentiation and functional maturation from human peripheral blood CD14+ monocytes,* 110(2) IMMUNOL LETT. 110-120 (2007). Changes in the expression level of a panel of surface molecules on Tα1-treated immature dendritic cells ("DC") demonstrated a direct effect of Tα1 on human CD14$^+$ monocyte to DC differentiation and activation by showing an increase in expression levels of several DC surface markers on differentiated iDCs and activated mDCs. A reduction in the effective endocytosis function of these iDCs, an enhancement in the activation of mDCs, and an elevated stimulation of allogeneic T cell proliferation was also observed. Most importantly, Tα1 induced the proliferating T Cells to release a broad spectrum of Th1 and Th2-type cytokines. Neither Tβ4 nor Tβ10, natural thymosins, had a similar effect in the assay.

ZADAXIN© was tested in a well-characterized SOD1$^{G93A}$ model of ALS. A statistically-significant reduction of ubiquitin in brain tissue and spinal cord was demonstrated on histopathology in the ZADAXIN®-treated mice. In a second model, Prp-TDP43$^{A315T}$, in which the overexpression of mutant TDP-43 under control of the mouse prion promoter, leads to a threefold overexpression of TDP-43 in the spinal cord and brain. The cohorts in the TDP-43 mouse model showed improvement in the growth and strength (based on wire hang tests) when treated with ZADAXIN©. Surprisingly, disease phenotype was prevented in one cohort. Interestingly, sudden death due to intestinal dysfunction can be observed in this model TDP-43 model. See S. Herdewyn et al., *Prevention of intestinal obstruction reveals progressive neurodegeneration in mutant TDP-43 (A315T) mice,* 9 MOLECULAR NEURODEGENERATION 24 (2014). Statistically-significant reduction in Iba1 and brain GFAP, measures of inflammation, were seen in the ZADAXIN®-treated mice.

Pathologies associated with ALS include hypermetabolism and inflammation. The role of mitochondria in cell function and homeostasis is through adenosine triphosphate ("ATP") production, calcium homeostasis, apoptosis signaling, and fatty acid oxidation which are possible thymic peptide targets. Mitochondria regulate cell metabolism through mitochondrial derived signaling and a process known as mitochondrial unfolded protein response. See L. Dupuis et al., *Mitochondria in Amyotrophic Lateral Sclerosis: A Trigger and a Target,* 1(6) NEURODEGENERATIVE DISEASES 245-254 (2004); S. Hill et al., *Role of Signaling Molecules in Mitochondrial Stress Response,* 9(225) FRONTIERS IN GENETICS 1-9 (2018); E-M. Eckl, *Sensing, signaling and surviving mitochondrial stress,* 78(16) CELLULAR AND MOLECULAR LIFE SCIENCES 5925-2951 (2021). In a multi-step pathway, misfolded proteins activate mitochondrial dysfunction through the expression of mitochondrial stress proteins that promote cell stress responses also known as the cell danger response. Mitochondria are complicit in modulating inflammation and the immune response through signaling factors. Damaged or dying cells release these factors into the extracellular environment, one of these factors is ATP. Damaged or fragmented mitochondrial DNA ("mtDNA") can evoke an immune response. Cascading responses activate ERK, p38, and Ikb pathways that culminate in upregulating inflammatory genes. Increased levels of mtDNA have been correlated with sporadic ALS. There is increasing evidence that inflammation accompanies or even precedes the death of motor neurons in ALS.

Therefore, TP-5 has multiple pharmacological effects suggestive of therapeutic utility including in diseases where inflammation plays a critical role such as ALS. However, TP-5, being an all natural, all-L pentapeptide, is subject to proteolytic cleavage and a short in vivo half life. TP-5 consists of the five L-amino acids Arg-Lys-Asp-Val-Tyr. The metabolic stability of TP-5 in mouse liver microsomes was determined to have a half-life of 23.1 minutes. Reversal of the orientation of the peptide bonds taken together with inversion of stereochemistry from the natural L- to the unnatural D- results in a high degree of topochemical equivalence between the parent peptide and its isomeric replacement, called the retro-inverso approach, while increasing metabolic stability against proteolysis. The full retro-inverso analog of TP-5 is the all-D amino acid sequence (D-Tyr)-(D-Val)-(D-Asp)-(D-Lys)-(D-Arg) (SEQ ID NO:1). See M. Chorev et al., *A dozen years of retro-inverso peptidomimetics,* 26 ACC. CHEM. RES. 266-273 (1993); Y. S Lee et al., Partial Retro-Inverso, Retro, and Inverson *Modifications of Hydrzide Linked Bifunctional Peptides for Opioid and Cholecystokinin (CCK) Receptors,* 50(1) J. MED CHEM. 165-168 (2007). The stability in mouse liver microsomes for the all-D amino acid sequence (D-Tyr)-(D-Val)-(D-Asp)-(D-Lys)-(D-Arg) (SEQ ID NO:1) was found to have a half-life of greater than 120 minutes.

Thus, there remains a need to harness the therapeutic utility of peptides such as TP-5 while increasing their in vivo half life.

SUMMARY OF THE INVENTION

A well-known regulator of purinome dynamics is thymopentin, the active pentapeptide of the homeostatic hormone thymopoietin. As people age thymopoietin decreases. Well-recognized as therapeutic, the half-life of exogenous thymopentin is seconds, severely limiting its use as a therapy. The inventor has developed the retro-inverso pentapeptide sequence of thymopentin (known as "TVALA™"), i.e., H-(D-Tyr)-(D-Val)-(D-Asp)-(D-Lys)-(D-Arg)-OH (SEQ ID NO:1) to decrease inflammation and rescue cells with dysregulated energy metabolism (that results in extracellular ATP), both conditions found in some ALS patients. The advantage of using a retro-inverso, D-peptide are techniques that extend the half-life of the thymopentin-active molecule, allowing the molecule to access the central nervous system and target dysregulated cells while leaving normal systems untouched.

ALS is one of a spectrum of diseases that may converge on common pathologies that could be treatable by ultimately regulating and slowing disease progression, such as neuroinflammation. Mitochondrial dysfunction is a prevalent feature of many neurodegenerative diseases, including motor neuron disorders such as ALS. Mitochondria play a central role in excitotoxicity, oxidative stress, and apoptosis but the link between pathology and mitochondrial stress remains undefined. See, e.g., L. Dupuis et al., *Mitochondria in Amyotrophic Lateral Sclerosis: A Trigger and a Target*, 1(6) NEURODEGENERATIVE DISEASES 245-254 (2004). Mitochondria and ATP signaling are at the heart of mechanisms that drive healing (Naviaux, personal communication 2022). There is substantial evidence that inflammation is associated with the death of motor neurons in ALS (see O. Komine et al., *Neuroinflammation in motor neuron disease*, 77(4) NAGOYA J. MED. SCI. 537-549 (2015)) and developing therapies that are neuroprotective are desired.

An embodiment of the invention is a method for ameliorating a neurodegenerative disorder in a subject suffering from said neurodegenerative disorder comprising administering to said subject an effective amount of a polypeptide comprising, in order from N-terminus to C-terminus, $$R\text{-}X_1\text{-}X_2\text{-}X_3\text{-}X_4\text{-}X_5\text{-}R'$$

wherein:
R is optionally 1-5 additional α-amino acids of either L-configuration or D-configuration;
$X_1$ is any amino acid of either L-configuration or D-configuration;
$X_2$ is any amino acid of either L-configuration or D-configuration;
$X_3$ is Asp or Glu of either L-configuration or D-configuration;
$X_4$ is any amino acid of either L-configuration or D-configuration;
$X_5$ is any amino acid of either L-configuration or D-configuration; and
R' is optionally 1-5 additional α-amino acids of either L-configuration or D-configuration,
with the proviso that at least three of $X_1$, $X_2$, $X_3$, $X_4$, and $X_5$ are of the D-configuration,
wherein the N-terminus is optionally modified by acetylation, and
wherein the C-terminus is optionally modified by amidation and/or methylation.

In certain embodiments of the method for ameliorating a neurodegenerative disorder in a subject suffering from said neurodegenerative disorder said neurodegenerative disorder is selected from the group consisting of amyotrophic lateral sclerosis (ALS), Alzheimer's Disease (AD), dysregulated mitochondrial energy metabolism, impaired neuromuscular regulatory function, and Parkinson's Disease (PD).

In certain embodiments of the method for ameliorating a neurodegenerative disorder in a subject suffering from said neurodegenerative disorder in said polypeptide $X_1$-$X_2$-$X_3$-$X_4$-$X_5$ is selected from the group consisting of:
D-Tyr-D-Val-D-Asp-D-Lys-D-Arg (SEQ ID NO:1),
D-Tyr-D-Val-D-Asp-D-Lys-D-Arg-NH$_2$ (SEQ ID NO:2),
Ac-D-Tyr-D-Val-D-Asp-D-Lys-D-Arg-NH$_2$ (SEQ ID NO:3),
D-Tyr-D-Val-D-Asp-D-Lys-D-Arg-NHMe (SEQ ID NO:4),
Ac-D-Tyr-D-Val-D-Asp-D-Lys-D-Arg-NHMe (SEQ ID NO:5), and
D-Tyr-D-Val-D-Asp-D-Lys-D-Asp-NH$_2$ (SEQ ID NO:7).

In an embodiment of the method for ameliorating a neurodegenerative disorder in a subject suffering from said neurodegenerative disorder in said polypeptide R is H, $X_1$ is D-Tyr, $X_2$ is D-Val, $X_3$ is D-Asp, $X_4$ is D-Lys, $X_5$ is D-Arg, and R' is OH (SEQ ID NO:1).

In certain embodiments of the method for ameliorating a neurodegenerative disorder in a subject suffering from said neurodegenerative disorder said polypeptide is administered intrathecally, intravenously, orally, and/or subcutaneously.

In certain embodiments of the method for ameliorating a neurodegenerative disorder in a subject suffering from said neurodegenerative disorder said polypeptide is administered in an amount ranging from 0.1 mg/kg of said subject to 50 mg/kg of said subject.

In certain embodiments of the method for ameliorating a neurodegenerative disorder in a subject suffering from said neurodegenerative disorder said polypeptide is administered in an amount ranging from 0.1 mg/kg of said subject to 10 mg/kg of said subject.

In certain embodiments of the method for ameliorating a neurodegenerative disorder in a subject suffering from said neurodegenerative disorder said polypeptide is administered in an amount ranging from 0.1 mg/kg of said subject to 1 mg/kg of said subject.

In certain embodiments of the method for ameliorating a neurodegenerative disorder in a subject suffering from said neurodegenerative disorder said polypeptide is lyophilized and reconstituted with an appropriate amount of diluent selected from the group consisting of distilled water and/or sodium chloride.

Another embodiment of the invention is a method for ameliorating an inflammatory disorder in a subject suffering from said inflammatory disorder comprising administering to said subject an effective amount of a polypeptide comprising, in order from N-terminus to C-terminus, $$R\text{-}X_1\text{-}X_2\text{-}X_3\text{-}X_4\text{-}X_5\text{-}R'$$

wherein:
R is optionally 1-5 additional α-amino acids of either L-configuration or D-configuration;
$X_1$ is any amino acid of either L-configuration or D-configuration;
$X_2$ is any amino acid of either L-configuration or D-configuration;

$X_3$ is Asp or Glu of either L-configuration or D-configuration;

$X_4$ is any amino acid of either L-configuration or D-configuration;

$X_5$ is any amino acid of either L-configuration or D-configuration; and

R' is optionally 1-5 additional α-amino acids of either L-configuration or D-configuration, with the proviso that at least three of $X_1$, $X_2$, $X_3$, $X_4$, and $X_5$ are of the D-configuration, wherein the N-terminus is optionally modified by acetylation, and wherein the C-terminus is optionally modified by amidation and/or methylation.

In certain embodiments of the method for ameliorating an inflammatory disorder in a subject suffering from said inflammatory disorder, said inflammatory disorder is selected from the group consisting of ankylosing spondylitis, chronic renal disease, Crohn's disease, dysregulated inflammatory response, hidradenitis suppurativa, inflammation, juvenile idiopathic arthritis, non-radiographic axial spondyloarthritis, non-infectious uveitis, neuroinflammation, plaque psoriasis, psoriasis, psoriatic arthritis, renal disease, rheumatoid arthritis, and ulcerative colitis. In certain embodiments of the method for ameliorating an inflammatory disorder in a subject suffering from said inflammatory disorder, said polypeptide $X_1$-$X_2$-$X_3$-$X_4$-$X_5$ is selected from the group consisting of:

D-Tyr-D-Val-D-Asp-D-Lys-D-Arg (SEQ ID NO:1),
D-Tyr-D-Val-D-Asp-D-Lys-D-Arg-NH$_2$ (SEQ ID NO:2),
Ac-D-Tyr-D-Val-D-Asp-D-Lys-D-Arg-NH$_2$ (SEQ ID NO:3),
D-Tyr-D-Val-D-Asp-D-Lys-D-Arg-NHMe (SEQ ID NO:4),
Ac-D-Tyr-D-Val-D-Asp-D-Lys-D-Arg-NHMe (SEQ ID NO:5), and
D-Tyr-D-Val-D-Asp-D-Lys-D-Asp-NH$_2$ (SEQ ID NO:7).

In certain embodiments of the method for ameliorating an inflammatory disorder in a subject suffering from said inflammatory disorder, in said polypeptide R is H, $X_1$ is D-Tyr, $X_2$ is D-Val, $X_3$ is D-Asp, $X_4$ is D-Lys, $X_5$ is D-Arg, and R' is OH (SEQ ID NO:1).

In certain embodiments of the method for ameliorating an inflammatory disorder in a subject suffering from said inflammatory disorder, said polypeptide is administered intrathecally, intravenously, orally, and/or subcutaneously.

In certain embodiments of the method for ameliorating an inflammatory disorder in a subject suffering from said inflammatory disorder, said polypeptide is administered in an amount ranging from 0.1 mg/kg of said subject to 50 mg/kg of said subject.

In certain embodiments of the method for ameliorating an inflammatory disorder in a subject suffering from said inflammatory disorder, said polypeptide is administered in an amount ranging from 0.1 mg/kg of said subject to 10 mg/kg of said subject.

In certain embodiments of the method for ameliorating an inflammatory disorder in a subject suffering from said inflammatory disorder, said polypeptide is administered in an amount ranging from 0.1 mg/kg of said subject to 1 mg/kg of said subject.

In certain embodiments of the method for ameliorating an inflammatory disorder in a subject suffering from said inflammatory disorder, said polypeptide is lyophilized and reconstituted with an appropriate amount of diluent selected from the group consisting of distilled water and/or sodium chloride.

BRIEF DESCRIPTION OF THE DRAWINGS

The foregoing will be apparent from the following more particular description of example embodiments of the invention, as illustrated in the accompanying drawings.

FIGS. 6A-6C show that the peptide TVALA™ (SEQ ID NO:1) used to pretreat A-375 melanoma cells did not rescue the cells against Erastin-induced cell death. FIG. 6D is the legend for FIGS. 6A-6C.

FIGS. 7A-7C show that the peptide TVALA™ (SEQ ID NO:1), pretreatment followed by incubation with peptide followed by Erastin, the cells were protected against Erastin-induced cell death. FIG. 7D is the legend for FIGS. 7A-7C.

DETAILED DESCRIPTION OF THE INVENTION

Figure 1:
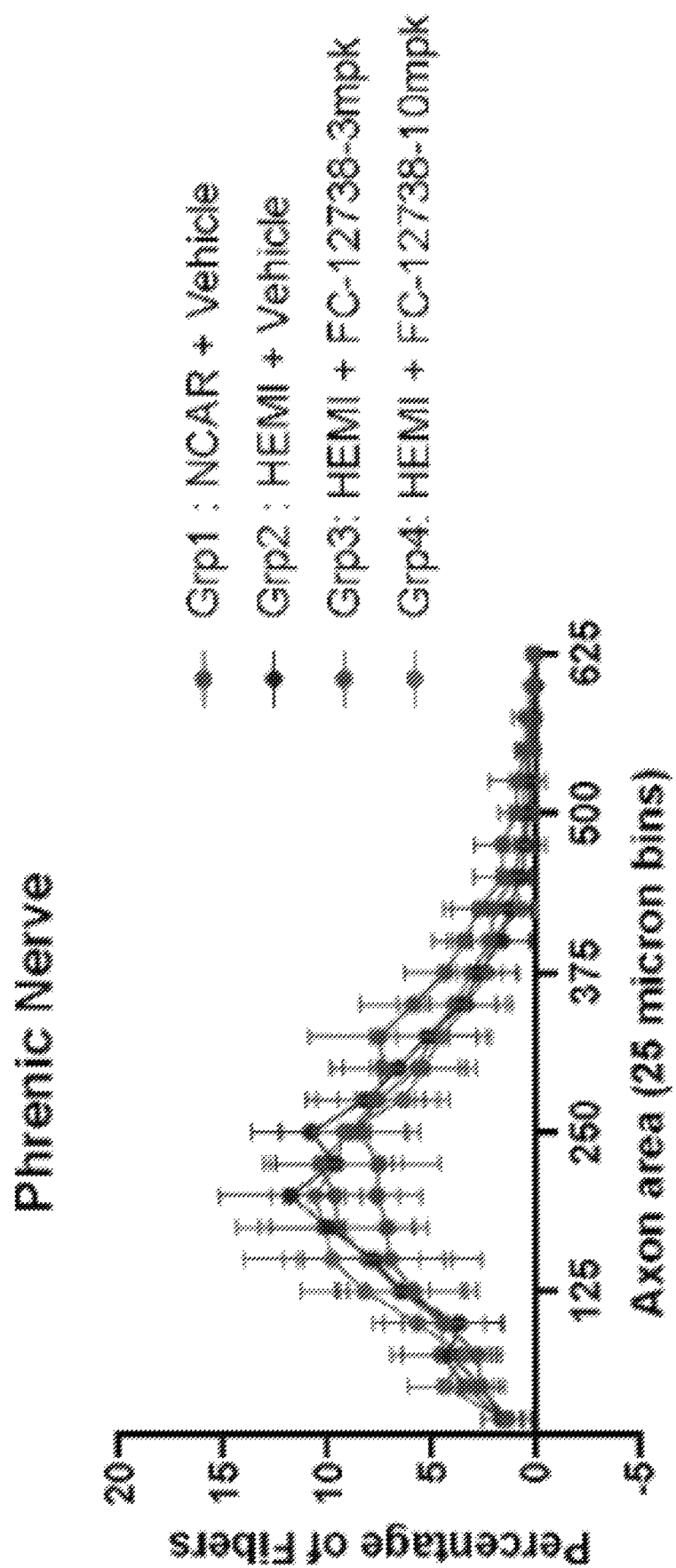
FIG. 1 shows that TVALA™ (SEQ ID NO:1) given at 10 mg/kg orally had smaller phrenic axons than vehicle treated mice.

The inventor has determined that polypeptides, including H-(D-Tyr)-(D-Val)-(D-Asp)-(D-Lys)-(D-Arg)-OH (SEQ ID NO:1), are valuable tools at ameliorating neurodegenerative and inflammatory disorders, including ALS, AD, PD, neurodegenerative disorders, inflammatory disorders (including ankylosing spondylitis, Crohn's disease, hidradenitis suppurativa, juvenile idiopathic arthritis, non-radiographic axial spondyloarthritis, non-infectious uveitis, plaque psoriasis, psoriasis, psoriatic arthritis, rheumatoid arthritis, and ulcerative colitis), and dysregulated mitochondrial energy metabolism.

The polypeptides comprise, in order from N-terminus to C-terminus,

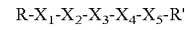

wherein:
R is optionally 1-5 additional α-amino acids of either L-configuration or D-configuration;
$X_1$ is any amino acid of either L-configuration or D-configuration;
$X_2$ is any amino acid of either L-configuration or D-configuration;
$X_3$ is Asp or Glu of either L-configuration or D-configuration;

X₄ is any amino acid of either L-configuration or D-configuration;

X₅ is any amino acid of either L-configuration or D-configuration; and

R' is optionally 1-5 additional α-amino acids of either L-configuration or D-configuration, with the proviso that at least three of $X_1$, $X_2$, $X_3$, $X_4$, and $X_5$ are of the D-configuration, wherein the N-terminus is optionally modified by acetylation, and wherein the C-terminus is optionally modified by amidation and/or methylation.

The Endoqenous Immune Modulator Thymopoetin and Thymopentin

The thymic hormone thymopoietin is an endogenous anti-inflammatory molecule with multiple actions in multiple tissues. The active part of the molecule is a pentapeptide, represented by the synthetic molecule thymopentin, that binds thymopoietin receptors. The central amino acid of the active pentapeptide and determines the bioactivity. See V. K. Singh et al., *Thymopentin and splenopentin as immunomodulators. Curent status,* 17(3) IMMUNOL. RES. 345-368 (1998).

Thymopoietin suppresses NF-kB activation, inhibits microglial activation by reducing secretion of inflammatory mediators, increases production of new oligodendrocytes generated from oligodendrocyte progenitor cells and assists their differentiation into mature myelinating oligodendrocytes. See C. Tuthill et al., *Thymosin Apha 1 —A Peptide Immune Modulator with a Broad Range of Clinical Applications,* 3(4) JOURNAL OF CLINICAL AND EXPERIMENTAL PHARMACOLOGY 1-17 (2013). The pro-molecule thymalfasin (Zadaxin®) is metabolized to the active pentapeptide thymopentin. See M. Severa et. al., *Thymosins in multiple sclerosis and its experimental models: moving from basic to clinical application,* 27 MULTIPLE SCLEROSIS AND RELATED DISORDERS 52-60 (2019). Thymopentin, Arg-Lys-Asp-Val-Tyr, that corresponds to positions 32-36 of thymopoietin, where it induces regulatory T cells and inhibits activated B cell differentiation and is a neurotropic factor.

TABLE 1

Comparison of three well-studied thymopoietin receptor molecules

| Thymopoietin | Thymalfasin | Thymopentin |
| --- | --- | --- |
| 49 amino acids | 28 amino acids | 5 amino acids |
| suppresses NF-kB activation | Treats hepatitis B and C | Inhibits B cell differentiation |
| inhibits microglial activation | Anti-inflammatory | Induces T regulatory cells |
| Reduces inflammatory mediators | Rescues stressed mitochondria | Reduces inflammatory mediators |
| Increases oligodendrocytes | Metabolized to thymopentin | Neurotropic factor |
| Assists differentiation of oligodendrocytes | Treats chemotherapy induced immunosuppression | The active part of thymopoietin |

See C. Tuthill et al., Thymosin Apha 1—A Peptide Immune Modulator with a Broad Range of Clinical Applications, 3(4) *JOURNAL OF CLINICAL AND EXPERIMENTAL PHARMACOLOGY* 1-17 (2013)

Thymopentin is the minimal sequence that reproduces the biological activities of thymopoietin and is an immunoregulatory molecule. Products containing thymopentin include Timunox©, Mepentil® and Sintomodulina® which are used for primary immunodeficiencies, secondary immunodeficiencies, in complications of cancer patients after chemotherapy, and for the stimulation of immune responses. Thymopentin is a soluble peptide hormone with pleiotropic effects. Both in vitro and in vivo studies have been conducted to show the multiple roles of thymopentin. See V. K. Singh et al., *Thymopentin and splenopentin as immunomodulators. Current status,* 17(3) IMMUNOL. RES. 345-368 (1998). Thymopentin demonstrated a dose dependent stimulation or inhibition of mitogen induced IgG, T cell proliferation, and enhanced synthesis of IL-2 in vivo. See J. Duchateau et al., *Immunomodulation with thymopentin: in vitro studies,* 6(1) MED. ONCOL. TUMOR PHARMACOTHER. 19-23 (1989); J. Duchateau et al., *In vitro influence of thymopentin on proliferative responses and phytohemagglutinin-induced interleukin 2 production in normal human lymphocyte cultures,* 4 SURVEY OF IMMUNOLOGIC RESEARCH 116-124 (1985). Additional in vivo mitogen induced responses include IFN production and enhanced NK cell activity in mice cells. See W. Diezel et al., *Induction and augmentation of mitogen-induced immune interferon production in human lymphocytes by a synthetic thymopoietin pentapeptide,* 43(6) BIOMED BIOCHIM ACTA. K9-K12 (1984); C. Hu et al., *In vivo enhancement of NK-cell activity by thymopentin,* 12(2) INTERNATIONAL JOURNAL OF IMMUNOPHARMACOLOGY 193-197 (1990).

Immunomodulatory actions from in vivo studies demonstrated thymopentin blocked neurotransmission and restored helper T cell activity. See M. C. Weksler et al., *Immunological studies of aging. IV. The contribution of thymic involution to the immune deficiencies of aging mice and reversal with thympoietin*32-36, 148(4) J. EXP. MED. 996-1006 (1978).

In renal dialysis patients thymopentin reduced IL-6, IL-8, TNF and CRP indicating that treatment notably reduced the inflammatory responses in the body and inhibit an acute phase response induced by end-stage renal disease. See Q. Zou et al., *The effect of thymopentin on immune function and inflammatory levels in end-stage renal disease patients with maintenance hemodialysis,* 14(1) AM. J. TRANSL. RES. 414-420 (2022). In the same study, thymopentin improved the state of oxidative stress by increasing the SOD, a major antioxidant enzyme that inhibits the accumulation of lipid peroxides.

Multiple studies on the safety of thymopentin found it "well tolerated even when administered concomitantly with a long list of drugs given for other reasons. The overall consensus is that thymopentin is a safe compound." See N. Friedmann, *Thymopentin: Safety overview,* 4 SURVEY OF IMMUNOLOGIC RESEARCH 139-148 (1985).

The Utility of ALS Mouse Models to Test Thymalfasin and Reactive Molecules

The transgenic mouse $SOD1^{G93A}$ is a toxic gain of function model that overexpresses the human SOD1 dismutase gene. The mice develop adult-onset neurodegeneration of spinal motor neurons and progressive motor deficits leading to paralysis. First reported in 1994, the G93A models are a cornerstone of preclinical ALS research despite the inability to translate efficacy in studies to effectiveness in humans. The model is useful to evaluate peripheral neuropathy using the femoral nerve. Ubiquitin in the brain and spinal cord are drugable targets and in this model ubiquitin ratio indicate impaired autophagy, not neuroinflammation. See C. Cheroni et al., *Accumulation of human SOD1 and ubiquitinated deposits in the spinal cord of SOD1G93A mice during motor neuron disease progression correlates with a decrease of proteasome,* 18(3) NEUROBIOL DIS. 509-522 (2005); B. Gong et al., *The Ubiquitin-Proteasome System: Potential Therapeutic Targets for Alzheimer's Disease and Spinal Cord Injury,* 9(Article 4) FRONTIERS IN MOLECULAR NEUROSCIENCE 1-16 (2016).

TAR DNA binding protein plays a crucial role in a growing set of neurodegenerative diseases including ALS. Supporting a central role of TAR DNA Binding Protein 43 in ALS, this protein links both familial and sporadic forms of ALS as mutations that are causative for disease and cytoplasmic aggregates are a hallmark of nearly all cases, regardless of TDP43 mutational status. See T. R. Suk et al., *The role of TDP-43 mislocalization in amytrophic lateral sclerosis*, 15:45 MOLECULAR NEURODEGENERATION 1-16 (2020). The forgoing supports investigating treatments affecting inflammation in the TDP43 mouse model. Astrocytes represent 30-40% of the cells in the CNS, form an integral part of the blood-brain barrier and establish numerous interactions with other cells in the nervous system including neurons. Astrocytes are central to the normal function of synapses and contribute to axonal metabolic maintenance through the regulation of ion homeostasis. See A. Abdelhak et al., *Blood GFAP as an emerging biomarker in brain and spinal cord disorders*, 18 NATURE REVIEWS NEUROLOGY 158-172 (2022). Glial fibrillary acidic protein ("GFAP") is the signature intermediate filament of astrocytes. The TDP43 transgenic mouse is useful to evaluate inflammation using GFAP levels and Iba1 ratios determined by histopathology.

Evidence that Thymalfasin May Target ALS Related Disease in ALS Mice

In mice, thymalfasin is metabolized to the active molecule thymopentin. Because mice process the pro-molecule thymalfasin into thymopentin as do humans, thymalfasin may illuminate the effects of thymopentin by increasing target engagement afforded by the pro-molecule. Two ALS mouse models, hemizygous B6.Cg-Tg(Prnp-TARDBP*A315T)95Balo/J male mice (JAX stock #010700) the SOD1$^{G93A}$ model and hemizygous B6SJL-Tg(SOD1*G93A)1Gur/J male mice were dosed with 0.04 mg/kg thymalfasin by subcutaneous (SQ) injection twice a week for 8 weeks as a 1.6 mg lyophilized powder in a 5 ml vial reconstituted with sterile water. Generally accepted markers in the SOD1$^{G93A}$ and TDP43 models that are associated with neurodegenerative disease include ubiquitin ratio in brain and spinal cord, GFAP, and Iba1. Significant observations in thymalfasin treated ALS mice are shown in Table 2.

TABLE 2

Significant observations in studies using thymalfasin in two ALS mouse models

| Significant observations | SOD1$^{G93A}$ model | TDP43 model |
|---|---|---|
| Ubiquitin ratio spinal cord | + | |
| Ubiquitin ratio brain | ++ | |
| Brain GFAP ratio | | ++ |
| Brain Iba1 | | ++ |

Definitions

All definitions of substituents set forth below are further applicable to the use of the term in conjunction with another substituent. Unless defined otherwise, all technical and scientific terms used herein have the same meaning as commonly understood by one of ordinary skill in the art to which this invention belongs.

As used herein, the singular forms "a," "and," and "the" include plural reference unless the context clearly dictates otherwise. Additionally, the term "comprises" is intended to include embodiments where the method, apparatus, composition, etc., consists essentially of and/or consists of the listed steps, components, etc. Similarly, the term "consists essentially of" is intended to include embodiments where the method, apparatus, composition, etc., consists of the listed steps, components, etc.

As used herein, the term "about" refers to a number that differs from the given number by less than 15%. In other embodiments, the term "about" indicates that the number differs from the given number by less than 14%, 13%, 12%, 11%, 10%, 9%, 8%, 7%, 6%, 5%, 4%, 3%, 2%, or 1%.

As used herein, the term "administration" is intended to include, but is not limited to, the following delivery methods: topical, oral, sub-lingual, buccal, parenteral, subcutaneous, transdermal, transbuccal, intravascular (e.g., intravenous or intra-arterial), intramuscular, subcutaneous, intranasal, and intra-ocular administration. Administration can be local at a particular anatomical site, such as a site of infection, or systemic.

Arg represents arginine, and is a residue of the amino acid arginine.

Asp represents aspartic acid, and is a residue of the amino acid aspartic acid.

"Configuration," as used herein, refers to the orientation of the amino group in a given polypeptide. The term "D-configuration" refers to a stereoisomer of a particular amino acid whose amino group is on the right side in its Fisher projection. The term "L-configuration" refers to a stereoisomer of a particular amino acid whose amino group is on the left side in its Fisher projection. If no configuration is listed herein, the L-configuration is to be presumed.

When used herein, a dose range reflected as two numbers means those doses as well as all doses within that range. For example, a dose range from 10 mg-11 mg means 10.0 mg, 10.05 mg, 10.10 mg, 10.15 mg, 10.20 mg, 10.25 mg, 10.30 mg, 10.35 mg, 10.40 mg, 10.45 mg, 10.50 mg, 10.55 mg, 10.60 mg, 10.65 mg, 10.70 mg, 10.75 mg, 10.80 mg, 10.85 mg, 10.90 mg, 10.95 mg, 11.00 mg, as well as any and all amounts therein, such as 10.34 mg, 10.78 mg, etc.

The phrase "effective amount" means an amount of an agent that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

A human subject may be an adult or a child. As used herein, a "child" refers to a human subject who is between the ages of 1 day to 17 years of age. The term "adult" refers to a human subject who is 18 years of age or older.

As used herein, a subject is "in need of" a treatment if such human or non-human animal subject would benefit biologically, medically, or in quality of life from such treatment (preferably, a human).

As used herein, the term "inhibit," "inhibition," or "inhibiting" refers to the reduction or suppression of a given condition, symptom, or disorder, or disease, or a significant decrease in the baseline activity of a biological activity or process.

As used herein, the terms "subject," "patient," and "individual" are used interchangeably and refer to a human of any age or gender.

As used herein, the term "treat," "treating," or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the subject. In yet another embodiment, "treat," "treating," or "treatment" refers to modulating the disease or disorder, either physically, (e.g., stabilization of a discernible symptom), physiologically, (e.g., stabilization of a physical parameter), or both. In yet another embodiment, "treat," "treating," or "treatment" refers to prophylaxis (preventing or delaying the onset or development or progression of the disease or disorder).

Lys represents lysine, and is a residue of the amino acid lysine.

As used herein, "nucleotide sequence" or "nucleic acid sequence" refers to an oligonucleotide sequence or polynucleotide sequence and variants, homologues, fragments, and derivatives thereof. The nucleotide sequence may be of genomic, synthetic, or recombinant origin and may be double-stranded or single-stranded, whether representing the sense or anti-sense strand. As used herein, the term "nucleotide sequence" includes genomic DNA, cDNA, synthetic DNA, and RNA.

"Pharmaceutically-acceptable carrier" means non-therapeutic components that are of sufficient purity and quality for use in the formulation of a composition of the invention that, when appropriately administered, typically do not produce an adverse reaction, and that are used as a vehicle for a drug substance.

The phrase "pharmaceutically-acceptable" indicates that the substance or composition must be compatible chemically and/or toxicologically, with the other ingredients comprising a formulation, and/or the mammal being treated therewith.

Pharmaceutical formulations include "pharmaceutically-acceptable" and "physiologically-acceptable" carriers, diluents, or excipients. In this context, the terms "pharmaceutically-acceptable" and "physiologically-acceptable" include solvents (aqueous or non-aqueous), solutions, emulsions, dispersion media, coatings, isotonic and absorption promoting or delaying agents, compatible with pharmaceutical administration. Such formulations can be contained in a liquid; emulsion, suspension, syrup, or elixir, or solid form; tablet (coated or uncoated), capsule (hard or soft), powder, granule, crystal, or microbead. Supplementary compounds (e.g., preservatives, antibacterial, antiviral, and antifungal agents) can also be incorporated into the compositions.

As used herein, "polypeptide" is used interchangeably with the terms "amino acid sequence," "peptide," and/or "protein."

Tyr represents tyrosine, and is a residue of the amino acid tyrosine.

Val represents valine, and is a residue of the amino acid valine.

EXAMPLES

Materials and Methods: The peptides used in the following examples were prepared using standard solid-phase and solution-phase peptide synthesis using techniques well-known in the art. See, e.g., Gregg Fields, *Introduction to Peptide Synthesis*, CURRENT PROTOCOLS IN PROTEIN SCIENCE (February 2002).

Example 1—TVALA™ Improves Target Engagement

Thymopentin ("TP-5") is a natural, all-L pentapeptide, that is subject to proteolytic cleavage and a short in vivo half-life. The stability in mouse liver microsomes for thymopentin is 23.1 minutes. See Table 3.

TABLE 3

A comparison of stability of natural thymopentin, TP-5, and TVALA ™ dosed in mice IV (intravenous), SC (subcutaneous), and PO (orally)

| Compound | Mouse Plasma Stability $t\frac{1}{2}$ (min) | Mouse Microsomal Stability $t\frac{1}{2}$ (min) | IV $t\frac{1}{2}$, mice (min) | SC $t\frac{1}{2}$, mice (min) | PO $t\frac{1}{2}$, mice (min) | SC % F, mice | PO % F, mice | SC Cmax (ng/mL) | PO Cmax (ng/ml) | SC AUCinf hr * ng/mL | PO AUCinf hr * ng/ml |
|---|---|---|---|---|---|---|---|---|---|---|---|
| TP-5 | 23.1 | >60 | 5.58 | 8.92 | 7.72 | 39 | 36 | 133 | 1367 | 126 | 1274 |
| TVALA ™ | >120 | >60 | 6.22 | 11.9 | 7.36 | 52 | 30 | 674 | 5291 | 355 | 2400 |

Reversing the orientation of the peptide bonds taken together with inversion of the stereochemistry from the natural L- to the unnatural D- (TVALA™) (SEQ ID NO:1) results in a high degree of topochemical equivalence between the parent peptide and its isomeric replacement. By maintaining the topochemical equivalence the bioactivity of the molecule is maintained. This retro-inverso approach increases the metabolic stability against proteolysis, the stability in mouse liver microsomes has a half-life of over 120 minutes. See Table 3. The increased metabolic stability was also observed in rat and dog microsomes. See Table 4.

TABLE 4

Stability of TVALA ™ in mouse, rat, and dog microsomes. % F = % oral bioavailability

| | Microsomal Stability (min) | Plasma Stability (min) | % F (PO) | % F (SC) | PO t½ (hrs) | SC t½ (hrs) | IV t½ (hrs) | B:P ratio |
|---|---|---|---|---|---|---|---|---|
| Mouse | >60 | >120 | 30 | 52 | 7.4 | 11.9 | 6.2 | 0.03- |
| Rat | >60 | | 6.7 | 79.2 | 9.6 | 5.7 | 6.8 | 0.06 |
| Dog | >60 | | 4.9 | | 3.5 | | | |

Example 2—TVALA™ Effects in ALS Animal Models

A 6-week efficacy testing of test article, TVALA™, in daily drinking water, in the SOD1$^{G93A}$ mouse model of ALS, with neurological scoring, neuroinflammation and axonopathy outcome measures was conducted by orally dosing with 3 mg/kg or 10 mg/kg. In phrenic nerves the axons numbers are not affected at this age, however axons start to atrophy, in femoral nerves, the mice lose axons and the remaining ones are atrophied.

Figure 2:
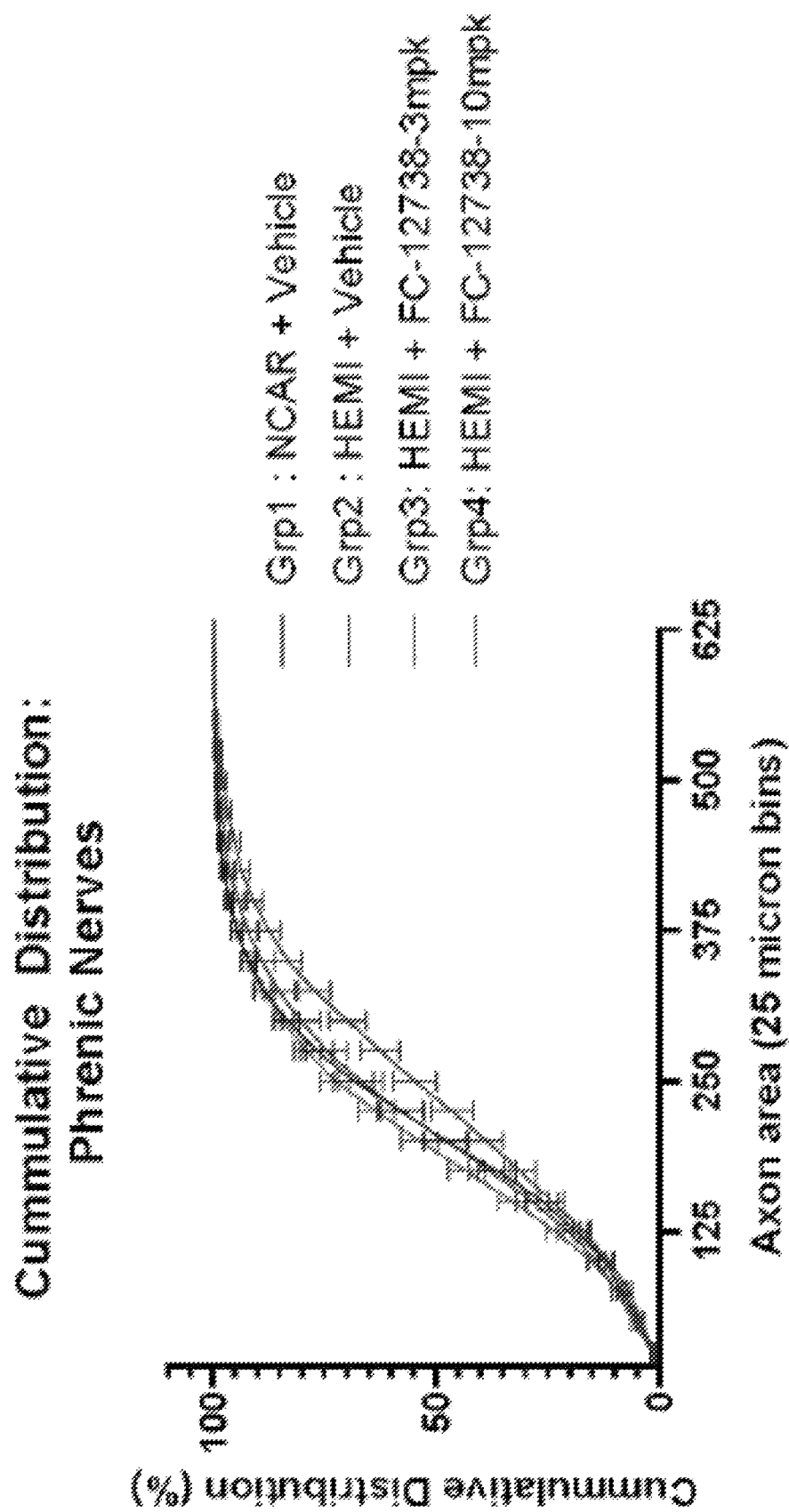
FIG. 2 shows that TVALA™ (SEQ ID NO:1) given at 10 mg/kg orally had smaller phrenic axons than vehicle treated mice.
Figure 3:
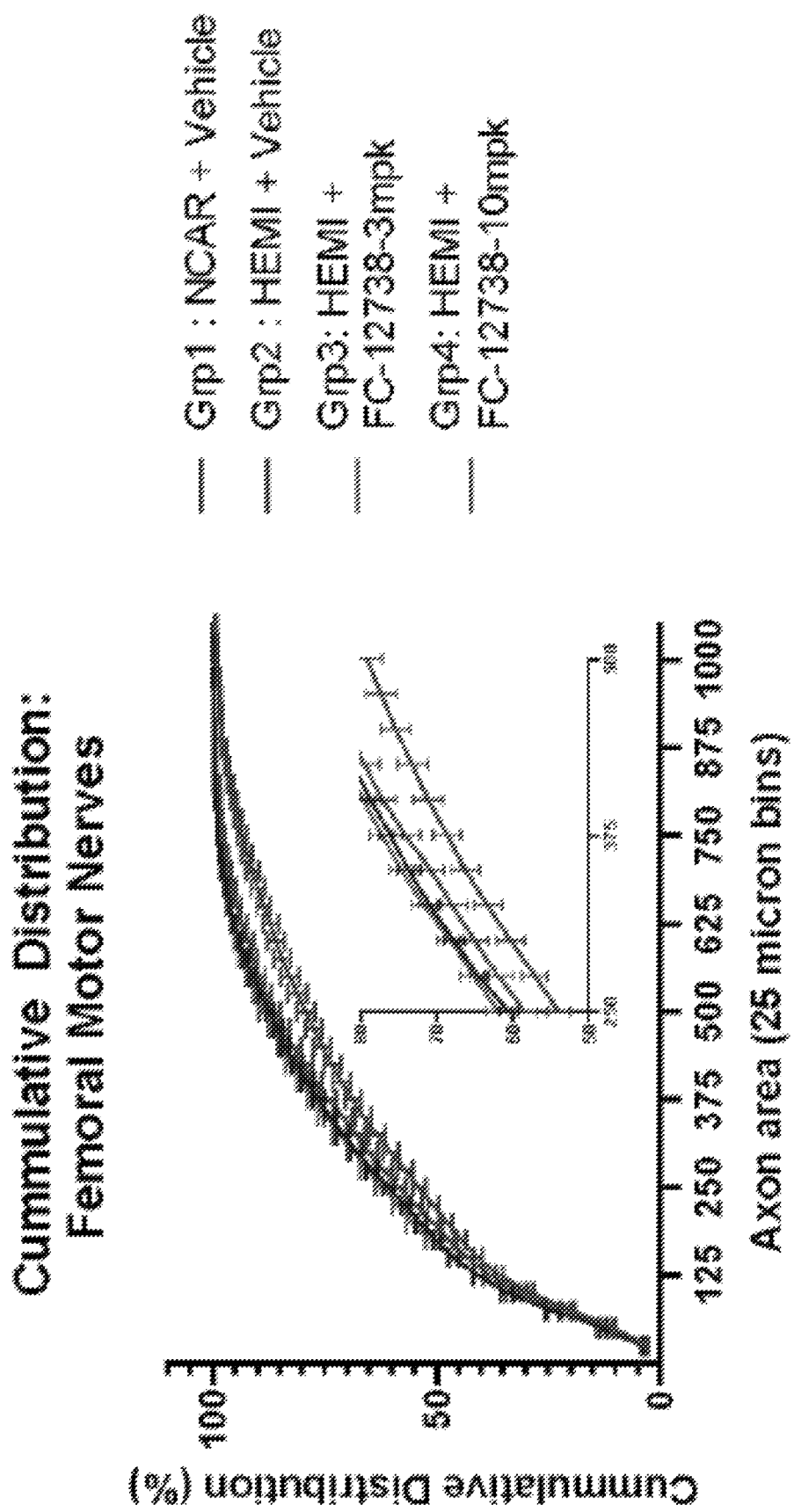
FIG. 3 shows that TVALA™ (SEQ ID NO:1) given at 3 mg/kg orally had slightly larger femoral motor axons than vehicle treated mice.
Figure 4:
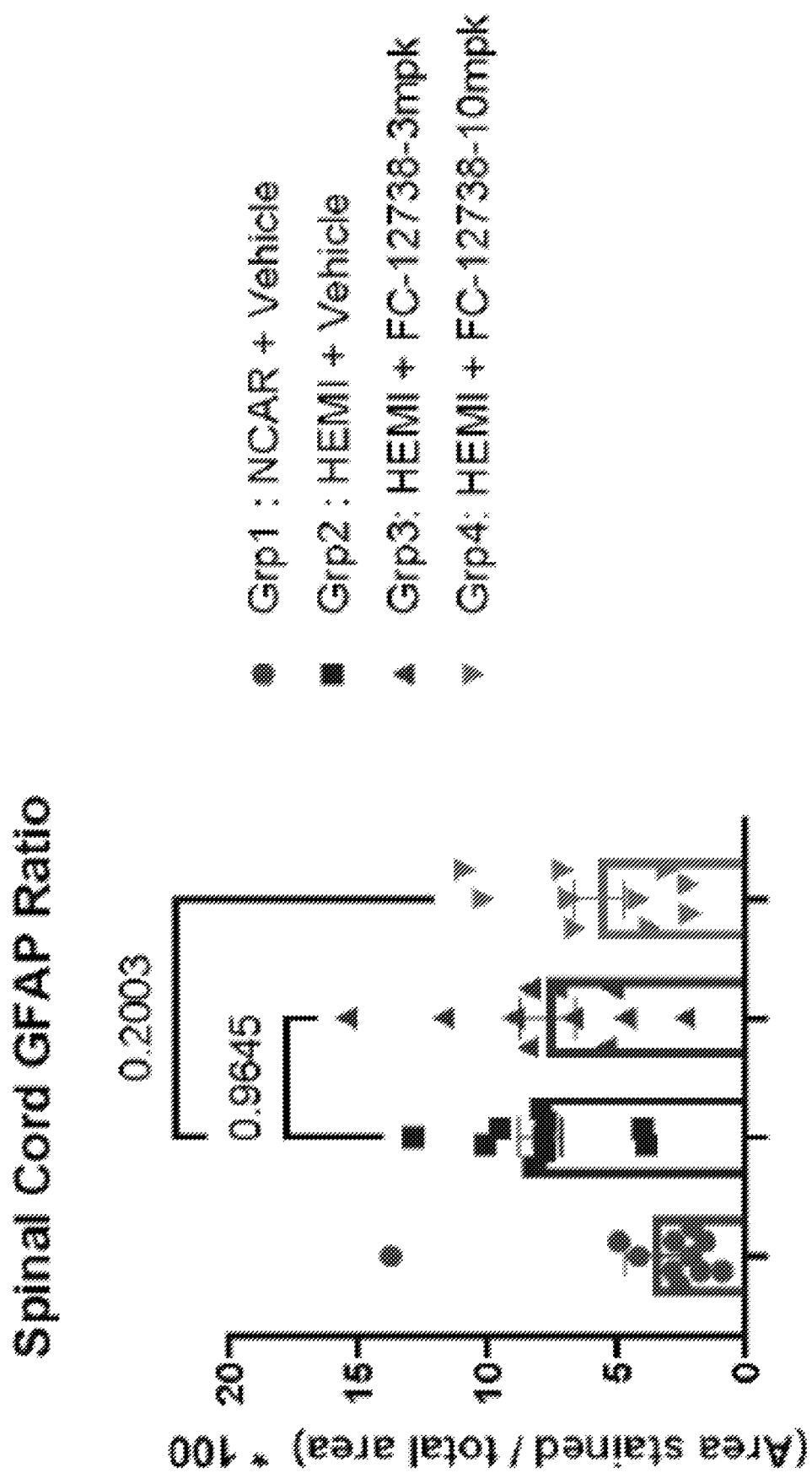
FIG. 4 shows that TVALA™ (SEQ ID NO:1) given at 3 mg/kg orally had more significant effects than 10 mg/kg orally on the neuroinflammatory marker GFAP demonstrating the biphasic action of a neurotropic molecule.

There was very discrete neuroprotection by the 3 mg/kg dose on the phrenic and femoral motor axon sizes (see FIG. 1), the observation was significant from a statistic point of view but the effect is small. The significant results are shown in Table 5. In this study hemizygous mice had fewer femoral axons, wild type mice have mostly larger phrenic nerve axons than untreated hemizygous mice, while 10 mg/kg treated hemizygous mice showed the smallest axons (see FIG. 2). A significant treatment effect with hemizygous mice treated with 3 mg/kg was observed on the femoral motor axon size, treated mice had axons of slightly larger size. See FIG. 3. It is not unusual for neurotropic molecules to have biphasic actions and often with a lower dose being desired as shown in the spinal cord GFAP. See FIG. 4.

These results indicate a low dose may be preferred over a higher dose. Also, brain inflammation was not impacted with oral administration of TVALA™ in this study, data not shown. The expected impact of the oral drug on the central nervous system was 5% based on in vivo testing (see Table 4). These results indicate the preferred administration is by sub-cutaneous injection to increase the bioavailability of the drug.

TABLE 5

Significant results in TVALA ™ treated SOD1$^{G93A}$

| Observations | SOD1$^{G93A}$ model 3 mg/kg TVALA ™ | SOD1$^{G93A}$ model 10 mg/kg TVALA ™ |
|---|---|---|
| Phrenic nerve cross-section area | | Smaller axons than control (FIG. 1) |
| Femoral motor axon size | Slightly larger than controls (FIG. 3) | |
| Spinal cord GFAP | | Mild sign, better than 3 mg/kg |

Example 3—Mitogen-Induced Blastogenic Response Assay of Peripheral Blood Mononuclear Cells (PBMCs) Assess Innate Cellular Immunity The influence of proinflammatory cytokines on the immunoregulatory function of immune cells from healthy donors may be assessed using mitogen-stimulated PBMC responses, which can be measured by determining the effect of test compounds on cytokine levels after stimulation by Concanavilin A ("ConA"). See Arneth, CURRENT PROTOCOLS IN CYTOMETRY 6.28 supplement 51 (2010); A. Erhardt et al., *Immunology and Liver Disease Karger* (2010); W. Ge et al., INTERNATIONAL IMMUNOPHARMACOLOGY 85 (2020); S. Malchow et al., BICHIMICA ET BIOPHYSICA ACTA 1812:290-301 (2011); A. Thomazelli et al., IMMUNOPHARMACOLOGY AND IMMUNOTOXICOLOGY, 40:5:387-392 (2018); N. Umeda et al., *LEUKOCYTE BIOLOGY* 791-801 (2019); H. Wang et al., WORLD JOURNAL OF GASTROENTEROLOGY 119-125 (2012).

Normal human PBMCs were stimulated with 5 μg/mL ConA for 72 hours followed by treatment with test compound, each of which are set forth in Table 6, at either 4.15 μM or 41.5 μM. Data represents mean of either TNFα or interleukin IL-6 lowering after ConA stimulation±SD. 2-way ANOVA with Dunnet's multiple comparison test; * $p<0.05$ (represented as +);  $p<0.01$ (represented as ++); * $p<0.001$ **** (represented as +++); $p<0.0001$ (represented as ++++); N=3 replicates. Both TNFα and IL-6 are inflammatory cytokines for which the lowering would be expected to provide therapeutic benefit for a variety of diseases. For example, TNFα is implicated in the inflammation associated with neurodegenerative and inflammatory disorders (see, e.g., G. D. Kalliolias et al., *TNF biology, pathogenic mechanisms and emerging therapeutic strategies*, 12(1) NATURE REVIEWS RHEUMATOLOGY 49-62 (2016)) as is IL-17 (see, e.g., S. Kaur et al., *A panoramic review of IL-6: Structure, pathophysiological roles and inhibitors*, 28(5) BIOORG. MED. CHEM. 115327 (2020)).

TABLE 6

Effect of Test Compounds on the Level of IL-6 and TNFα Lowering in ConA Stimulated Peripheral Blood Mononuclear Cells

| # | Test compound | Molecular Weight determined (daltons) | Concentration of test compounds (μM) | | | |
|---|---|---|---|---|---|---|
| | | | IL-6 | | TNFα | |
| | | | 4.15 | 41.5 | 4.15 | 41.5 |
| 1 | L-Arg-L-Lys-L-Asp-L-Val-L-Tyr ("TP-5") (SEQ ID NO: 6) | 680.3 | + | +++ | +++ | ++++ |
| 2 | D-Tyr-D-Val-D-Asp-D-Lys-D-Arg (SEQ ID NO: 1) | 680.3 | ++ | +++ | ++ | ++ |
| 3 | D-Tyr-D-Val-D-Asp-D-Lys-D-Asp-NH$_2$ (SEQ ID NO: 7) | 638.2 | − | +++ | + | ++ |
| 4 | Ac-D-Tyr-D-Val-D-Asp-D-Lys-D-Arg-NH$_2$ (SEQ ID NO: 3) | 721.3 | + | ++ | ++ | +++ |
| 5 | D-Tyr-D-Val-D-Asp-D-Lys-D-Arg-NHMe (SEQ ID NO: 4) | 693.3 | + | ++ | − | + |
| 6 | Ac-D-Tyr-D-Val-D-Asp-D-Lys-D-Arg-NHMe (SEQ ID NO: 5) | 735.3 | + | ++++ | ++++ | ++++ |

Example 4—TVALA™ Effects Purinergic Signaling In In Vitro Stressed ALS-Derived Adipose Stem Cells Cells derived from ALS patient tissues exhibit hallmark metabolic defects that can be rescued when tested in vitro. See J-H. Hor et al., *ALS motor neurons exhibit hallmark metabolic defects that are rescued by SIRT3 activation*, 28 CELL DEATH & DIFFERENTIATION 1379-1397 (2021). Adipose stem cells ("ASCs") derived from fat tissue harvested from an ALS patient were glycolytic showing increased proliferation and lipid accumulation in culture. An in vitro model of mitochondrial dysfunction was initiated with ALS patient derived ASCs grown in growth media. After cells were confluent, the growth media was treated with chemical stressors, such as ionomycin. Ionomycin induces cell death, apoptosis, peroxide formation, extracellular ATP, and peroxynitrites that are related to mitochondrial dysfunction. The media was exchanged and replaced with basic DMEM with 4 mM pyruvate and no additional growth factors. Test compounds were added in an effort to rescue the ionomycin treated cells. After recovery, 6 hours, the cells were measured for viability, apoptosis, peroxides, and peroxynitrites by SeaHorse analysis. The ASC patient derived cells are a good model to investigate dysregulated mitochondrial dysfunction in disease, these effects are not apparent in all ALS patient derived iPSC fibroblast cells (data not shown).

Figure 5:
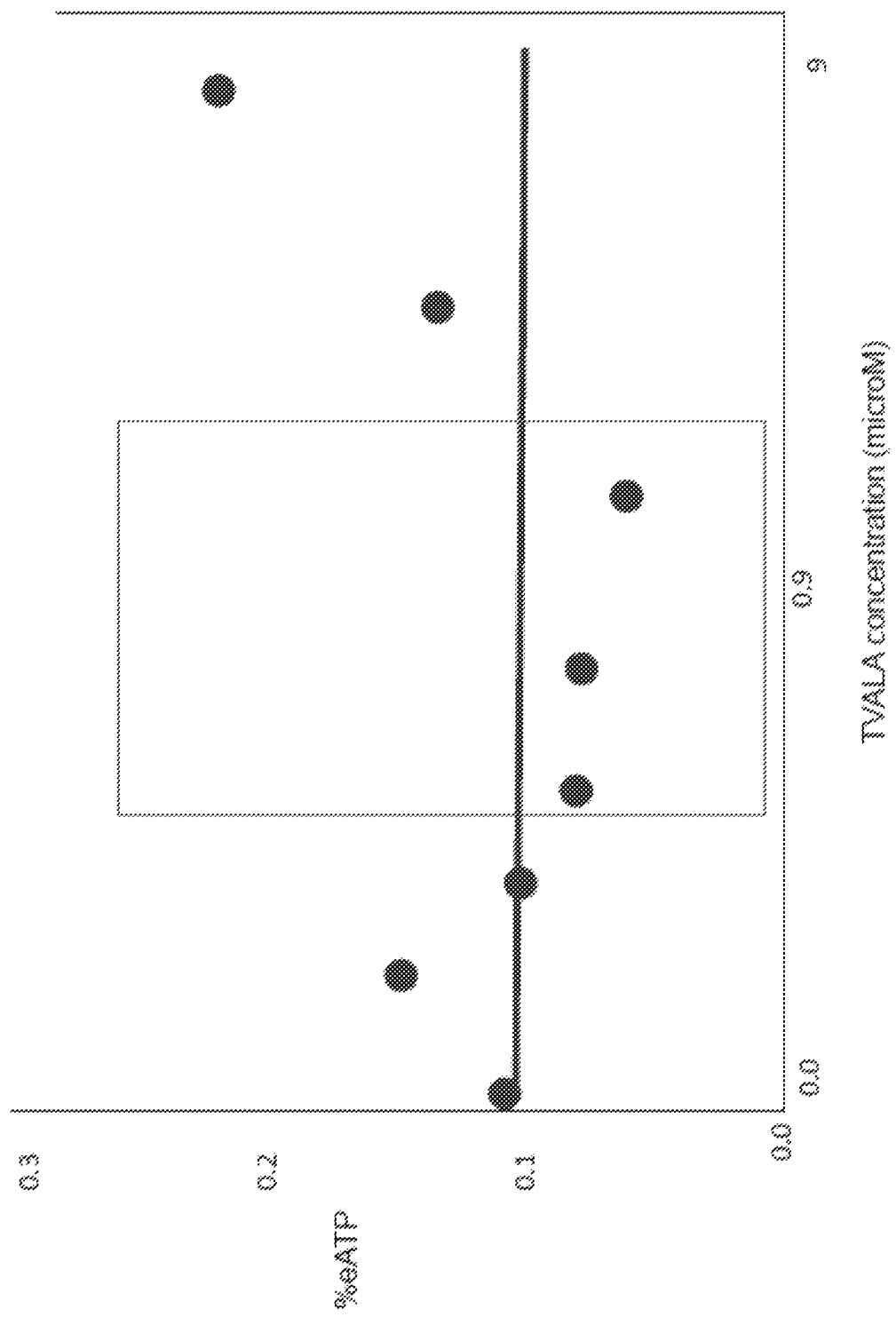
FIG. 5 shows that TVALA™ (SEQ ID NO:1) decreased extracellular ATP, eATP (circle) in in vitro cultured adipose stem cells ("ASC") from an ALS patient. The horizontal line indicates the dysfunctional levels in untreated cells, the box indicates the desired concentration of TVALA™ that rescues the mitochondria in ALS-ASCs. The X axis is TVALA™ concentration and the Y axis is % eATP.
Figure 6A:
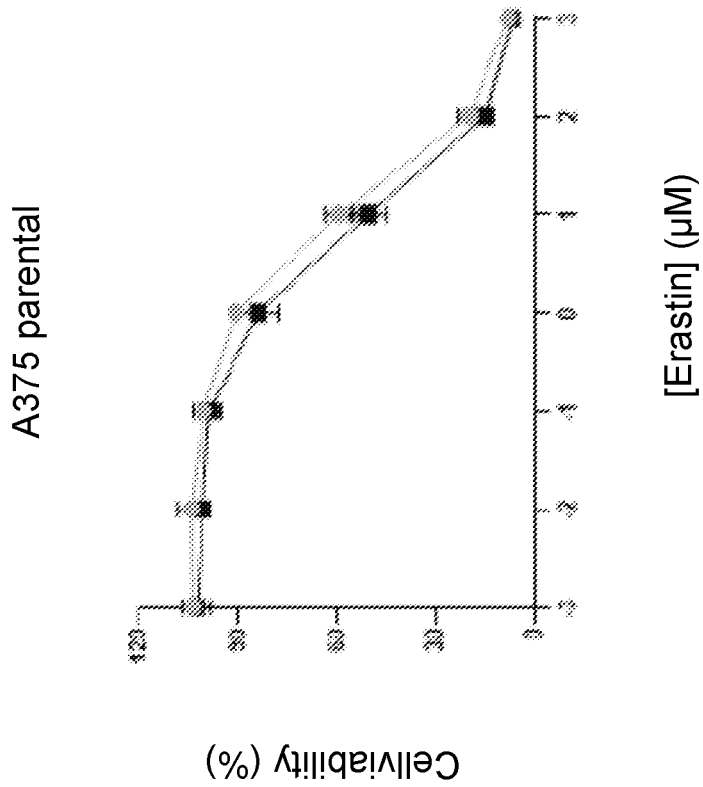
Figure 6B:
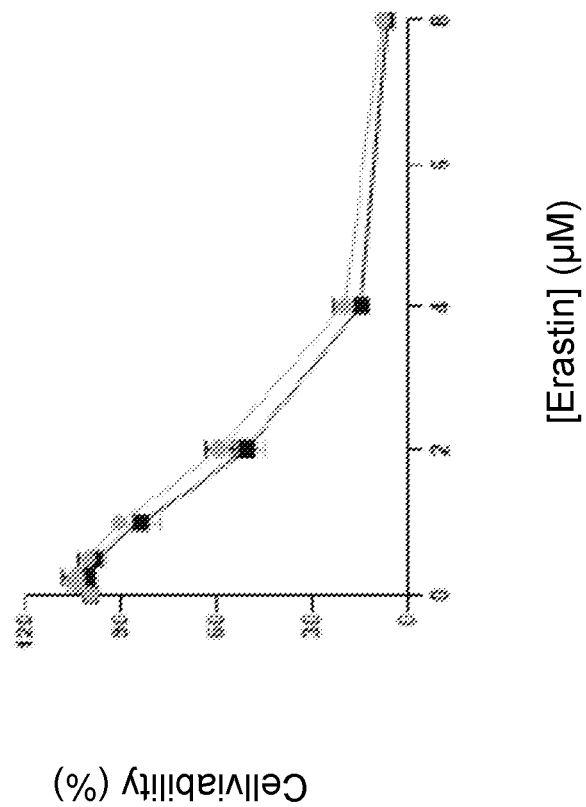

Results of the analysis showed that ALS-ASC cells were hypermetabolic and retained lipids. The TVALA™ treatment reduced peroxides and decreased extracellular ATP ("eATP"). See FIG. 5 (the line indicates a reduction of eATP with TVALA™). The eATP inhibition in this assay is expected to be pluribeneficial because purinergic signaling targets common responses in neurodegenerative disease, normalizing a dysregulated eATP may slow the progress of disease such as ALS). As stated previously, the complex cellular cross-talk occurring in ALS and the recognized function of extracellular nucleotides and adenosine in neuroglia communication, the ability of TVALA™ to restoring purinome dynamics is beneficial in an ALS patient to slow the progression of disease as demonstrated in vitro.

Example 5—Effect of TVALA™ on Erastin-Induced Ferroptotic Cell Death

Melanoma cell lines A-375, A-375 non-target, and A-375 (Prdx6 KO) cells were pre-incubated with TVALA™, washed, and treated with Erastin. Following treatment, the cells were evaluated for viability. Pretreatment with TVALA™ did not rescue the cells against Erastin-induced cell death. See FIGS. 6A-6D. When the cells were pre-treated with TVALA™, washed, and incubated with TVALA™ followed by treatment with Erastin, the cells were protected against Erastin-induced cell death. See FIGS. 7A-7D. When A-375 non target cells or A-375 knock out cells were used there was no effect of pre-treatment followed by TVALA™ treatment as expected (data not shown). The TVALA™ effect in the positive control assay, the A-375 cell line, demonstrates the ability to measure the effect of TVALA™ in blocking Erastin-induced ferroptosis in additional cell lines such as cultured neurons.

Example 6—D- but not L-Peptides have Significant Positive Effects

ALS patient-derived ASCs showing hypermetabolism and lipid sequestration were stressed and treated with peptides (shown below, column 2) and effect of the peptide measured with SeaHorse analytics. The results show that the D- but not the L-peptides had a significant positive effect. TVALA™ was superior to the other compounds.

TABLE 7

| Compound | Test compound | Test Range (DMSO/H$_2$O) | Conc. with positive effect | p value |
|---|---|---|---|---|
| 1 | Arg-Lys-Asp-Val-Tyr (TP-5) (SEQ ID NO: 6) | 0.01-100 mM | none | |

TABLE 7-continued

| Compound | Test compound | Test Range (DMSO/H₂O) | Conc. with positive effect | p value |
|---|---|---|---|---|
| 2 | Arg-Lys-Asp-Val-Tyr-NH₂ (SEQ ID NO: 8) | 5 mM | none | |
| 3 | Ac-Arg-Lys-Asp-Val-Tyr-NH₂ (SEQ ID NO: 9) | 0.5 mM and 5 mM | none | |
| 4 | Arg-Lys-Asp-Val-Tyr-NHMe (SEQ ID NO: 10) | 5 mM | none | |
| 5 | Ac-Arg-Lys-Asp-Val-Tyr-NHMe (SEQ ID NO: 11) | 5 mM | none | |
| 6 | D-Tyr-D-Val-D-Asp-D-Lys-D-Arg (SEQ ID NO: 1) | 5 mM | 5 mM | 0.0147 |
| 7 | D-Tyr-D-Val-D-Asp-D-Lys-D-Arg-NH₂ (SEQ ID NO: 2) | 0.5 mM and 5 mM | 0.5 mM | 0.0481 |
| 8 | Ac-D-Tyr-D-Val-D-Asp-D-Lys-D-Arg-NH₂ (SEQ ID NO: 3) | 0.5 mM and 5 mM | 5 mM | 0.0361 |
| 9 | D-Tyr-D-Val-D-Asp-D-Lys-D-Arg-NHMe (SEQ ID NO: 4) | 5 mM | | |
| 10 | Ac-D-Tyr-D-Val-D-Asp-D-Lys-D-Arg-NHMe (SEQ ID NO: 5) | 5 mM | | |

Example 7—TVALA™ is Steroid Sparing

TVALA™ may be steroid sparing in diseases that involve innate immunity and autoimmune components that are traditionally treated with steroids. For example, age-related macular degeneration is treated with steroid anti-inflammatory agents. TVALA™ is used as an adjunct to traditional therapies, decreasing or eliminating the need for steroids. Another example is for renal dialysis patients, for which TVALA™ is used as adjunctive or as a replacement to anti-inflammatory therapies. Elamipretide Triacetate is a small, mitochondrially-targeted d-tetrapeptide that is not entirely different from TVALA™, as both have two basic residues (Arg and Lys) and both have a d-Arg. Elamipretide triacetate appears to reduce the production of the toxic reactive oxygen species and stabilize cardiolipin to moderate mitochondrial disease. In vitro comparisons of Elamipretide triacetate and TVALA™ indicate TVALA™ has more target receptors and is superior at immunomodulation that the tetrapeptide (data not shown).

Example 8—TVALA™ is Useful in Assays, Including in Discovering Novel Biomarkers Evaluating the effect of TVALA™ in in vitro assays by incorporating patient derived cells and age/sex matched cells from clinically normal people as a control allow the evaluation of altered disease pathways. The identified factors that influence dysregulated pathways can reveal novel biomarkers. The lack of identifying biomarkers for neurodegenerative diseases to date point out that more dynamic and down-stream molecules need to be identified. In vitro assays incorporating patient cells allow a precision medicine approach. Using drugs such as TVALA™ in assay systems identify areas of interest and allow stratification of patients.

Example 9—TVALA™ Modulates Exosomes

Neurodegenerative diseases are closely related to brain function and the progression of the diseases are irreversible. Due to brain tissue being not easy to acquire, the study of the pathophysiology of neurodegenerative disorders has many limitations-lack of reliable early biomarkers and personalized treatment. At the same time, the blood-brain barrier ("BBB") limits most of the drug molecules into the damaged areas of the brain, which makes a big drop in the effect of drug treatment. Exosomes, types of endogenous nanoscale vesicles, play a key role in cell signaling through the transmission of genetic information and proteins between cells. Because of the ability to cross the BBB, exosomes are expected to link peripheral changes to CNS events as potential biomarkers, and can even be used as a therapeutic carrier to deliver molecules specifically to CNS. Exosomes have a role in pathophysiology, diagnosis, prognosis, and treatment of some neurodegenerative diseases (including Alzheimer's Disease, Parkinson's Disease, Huntington's Disease, and Amyotrophic Lateral Sclerosis).

Figure 8:
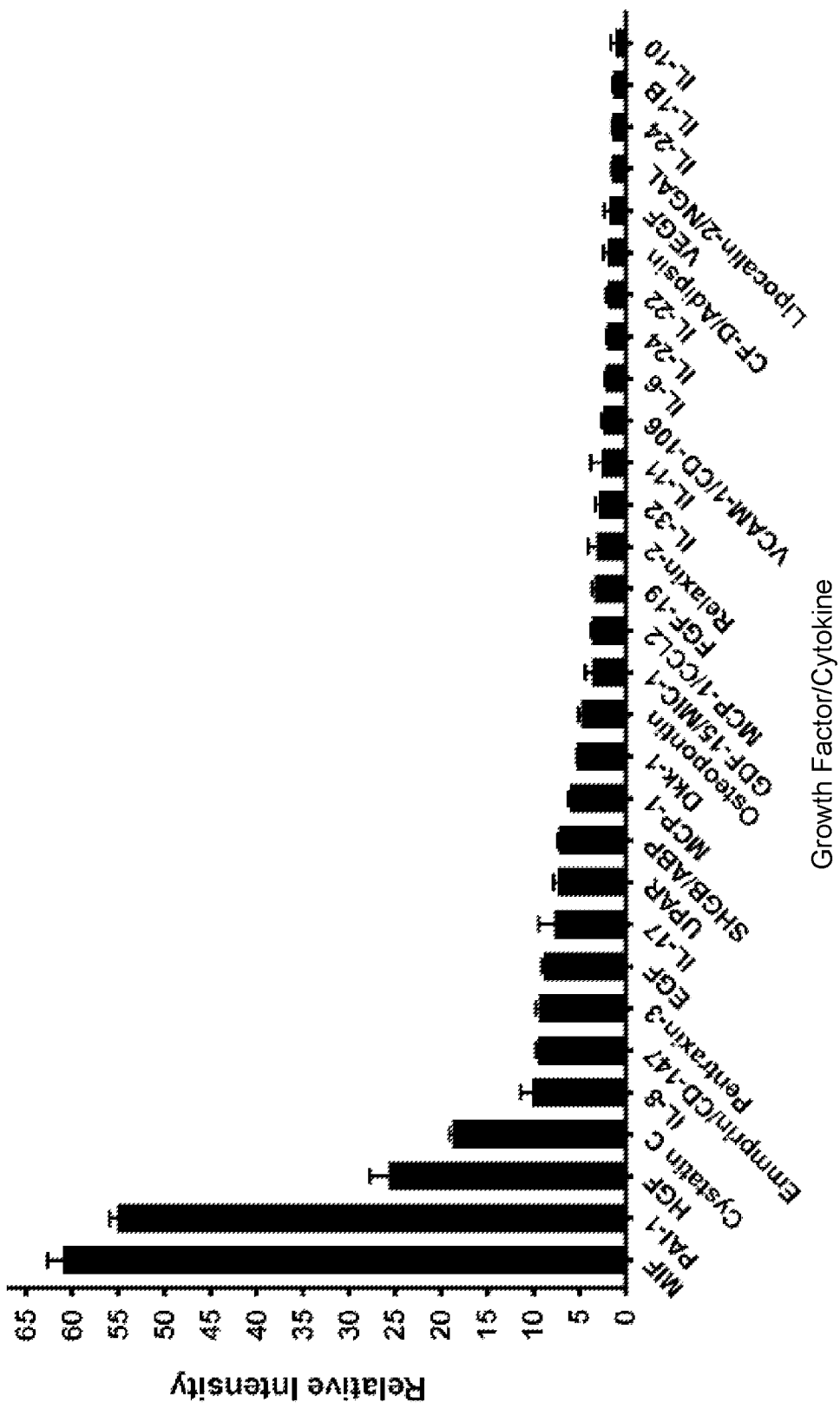
FIG. 8 shows 32 growth factors and cytokines in optimized culture media from adipose stem cells ("ASCs") from a healthy donor.
Figure 9:
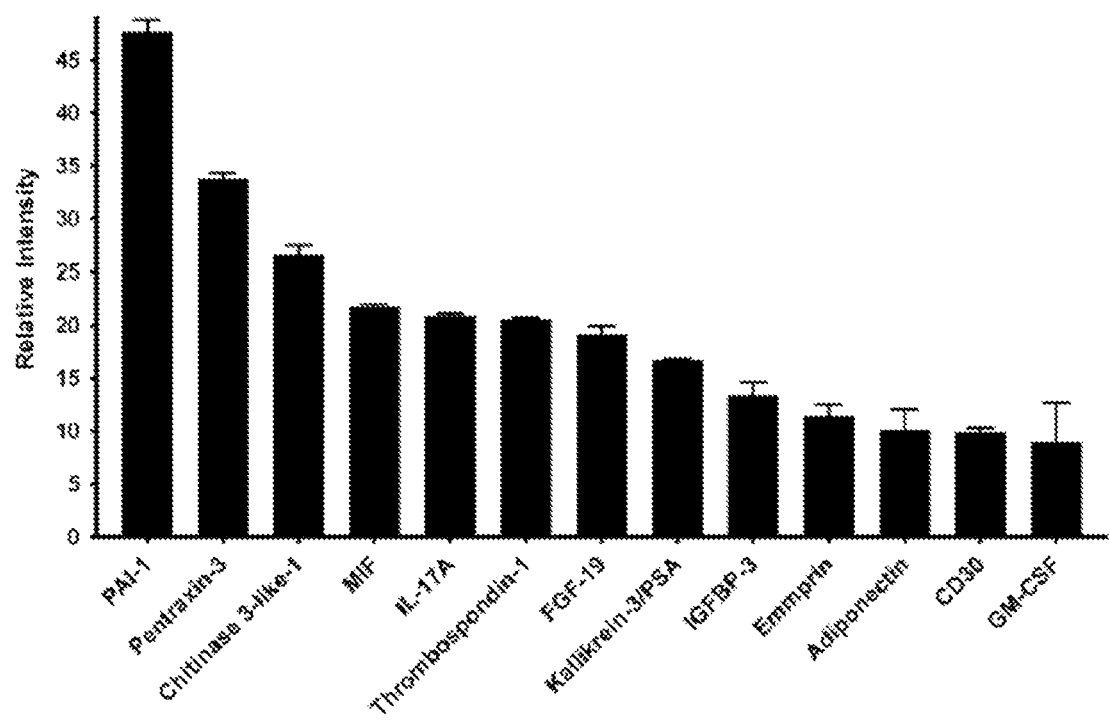
FIG. 9 shows growth factors and cytokines in optimized culture media from adipose stem cells ("ASCs") from an ALS patient.

Experiments show a similar profile of 32 growth factors and cytokines when culture media from adipose stem cells ("ASC"), dental pulp stem cells ("DPSC"), or mesenchymal stem cells ("MSC") sources are evaluated. A similar but not identical profile is seen in ASCs derived from clinically normal patients and ALS derived ASCs. See FIG. 8 (normal patients) and FIG. 9 (ASC-ALS derived cells). Various growth factor formulations are tested and optimized. Expression of ASC VEGF-A, VEGF-D, VEGFR2, and VEGFR3 expression is measured. The VEGF pathway is an active area of investigation concerning hypermetabolism in ALS patients.

| | ASC-CM | DPSC-CM | MSC-CM |
|---|---|---|---|
| Growth Factors | | | |
| G-CSF | √ | √ | √ |
| VEGF | √ | √ | √ |
| EGF | √ | √ | √ |
| PDGF-BB | √ | √ | √ |
| b-NGF | √ | √ | √ |
| FGFb | √ | √ | √ |
| IGF-1 | √ | √ | √ |
| TGF-b | √ | √ | √ |
| PlGF-1 | √ | √ | √ |
| Cytokines | | | |
| TNFa | √ | √ | √ |
| IFNγ | √ | √ | √ |
| GM-CSF | √ | √ | √ |
| IL-1a | √ | √ | √ |
| IL-8 | √ | √ | √ |
| IP-10 | √ | √ | √ |
| Rantes | √ | √ | √ |

|  | ASC-CM | DPSC-CM | MSC-CM |
|---|---|---|---|
| IL-6 | √ | √√ | √√√ |
| Resistin | √ | √ | √ |
| PAI-1 | √√ | √ | √√ |
| IL-12 | √ | √ | √ |
| IL-13 | √ | √ | √ |
| Eotaxin-3 | √ | √ | √ |
| SCF | √ | √ | √ |
| MCP-1 | √ | √√√ | √√ |
| MIP-1a | √ | √ | √ |
| IL-2 | √ | √ | √ |
| IL-4 | √ | √ | √ |
| IL-10 | √ | √ | √ |
| Leptin | √ | √ | √ |
| Adipo | √ | √ | √ |
| IL-17a | √ | √ | √ |
| IL-1b | √ | √ | √ |

Exosomes are membrane-bound extracellular vesicles. Exosomes can be diagnostic tools and cell signaling molecules. Exosomes can be a vehicle for drug delivery and therapy.

TVALA™ is incorporated into exosomes to exert beneficial effects in ALS. Adipose stem cell culture media is optimized for therapy in ALS. Exosomes from a commercial source are examined and compared to exosomes found in patients with neurodegenerative diseases. TVALA™ rescues dysregulated mitochondrial energy metabolism in vitro, reduces extracellular peroxides in vitro (see FIG. 5), and normalizes VEGFR2 expression of the ALS patient derived cells. TVALA™ is superior to TP-5 in this context. By incorporating TVALA™ into exosomes and administering the exosome-spiked ASC-CM to patients, the therapy normalizes functional pathways that are diseased in neurodegenerative diseases that follow a final common pathway (such as AD, ALS, Huntington's, and Parkinson's).

CONCLUSIONS

There are no ALS animal model systems that replicate the human phenotype. It is possible to use murine models to suggest target tissues to extrapolate to humans, however it is necessary to use in vitro assays from normal and ALS derived cells. The inventor's data shows using in vitro modeling that TVALA™ affects cytokine pro-and anti-inflammatory levels as well as rescuing purinergic signaling in dysregulated cells. These responses are related to maintaining neuronal/glial tissue homeostasis.

Embodiments

Embodiments of the invention include, but are not limited to, the following embodiment.

Embodiment 1: A polypeptide comprising, in order from N-terminus to C-terminus,

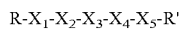

wherein:
R is optionally 1-5 additional α-amino acids of either L-configuration or D-configuration;
$X_1$ is any amino acid of either L-configuration or D-configuration;
$X_2$ is any amino acid of either L-configuration or D-configuration;
$X_3$ is Asp or Glu of either L-configuration or D-configuration;
$X_4$ is any amino acid of either L-configuration or D-configuration;
$X_5$ is any amino acid of either L-configuration or D-configuration; and
R' is optionally 1-5 additional α-amino acids of either L-configuration or D-configuration,
with the proviso that at least three of $X_1$, $X_2$, $X_3$, $X_4$, and $X_5$ are of the D-configuration,
wherein the N-terminus is optionally modified by acetylation, and
wherein the C-terminus is optionally modified by amidation and/or methylation.

Embodiment 2: The polypeptide of Embodiment 1, wherein said $X_1$-$X_2$-$X_3$-$X_4$-$X_5$ is selected from the group consisting of:
D-Tyr-D-Val-D-Asp-D-Lys-D-Arg (SEQ ID NO:1),
D-Tyr-D-Val-D-Asp-D-Lys-D-Arg-NH$_2$ (SEQ ID NO:2),
Ac-D-Tyr-D-Val-D-Asp-D-Lys-D-Arg-NH$_2$ (SEQ ID NO:3),
D-Tyr-D-Val-D-Asp-D-Lys-D-Arg-NHMe (SEQ ID NO:4),
Ac-D-Tyr-D-Val-D-Asp-D-Lys-D-Arg-NHMe (SEQ ID NO:5), and D-Tyr-D-Val-D-Asp-D-Lys-D-Asp-NH$_2$ (SEQ ID NO:7).

Embodiment 3: The polypeptide of Embodiment 1, wherein R is H, $X_1$ is D-Tyr, $X_2$ is D-Val, $X_3$ is D-Asp, $X_4$ is D-Lys, $X_5$ is D-Arg, and R' is OH (SEQ ID NO:1).

Embodiment 4: A composition comprising a polypeptide according to any one of Embodiments 1-3 and a pharmaceutically-acceptable carrier.

Embodiment 5: A method for ameliorating a neurodegenerative disorder in a subject suffering from said neurodegenerative disorder comprising administering to said subject an effective amount of a polypeptide comprising, in order from N-terminus to C-terminus,

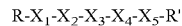

wherein:
R is optionally 1-5 additional α-amino acids of either L-configuration or D-configuration;
$X_1$ is any amino acid of either L-configuration or D-configuration;
$X_2$ is any amino acid of either L-configuration or D-configuration;
$X_3$ is Asp or Glu of either L-configuration or D-configuration;
$X_4$ is any amino acid of either L-configuration or D-configuration;
$X_5$ is any amino acid of either L-configuration or D-configuration; and
R' is optionally 1-5 additional α-amino acids of either L-configuration or D-configuration,
with the proviso that at least three of $X_1$, $X_2$, $X_3$, $X_4$, and $X_5$ are of the D-configuration,
wherein the N-terminus is optionally modified by acetylation, and
wherein the C-terminus is optionally modified by amidation and/or methylation.

Embodiment 6: The method according to Embodiment 5, wherein said neurodegenerative disorder is selected from the group consisting of amyotrophic lateral sclerosis (ALS), Alzheimer's Disease (AD), dysregulated mitochondrial energy metabolism, impaired neuromuscular regulatory function, and Parkinson's Disease (PD).

Embodiment 7: The method according to Embodiment 5, wherein said $X_1$-$X_2$-$X_3$-$X_4$-$X_5$ is selected from the group consisting of:

D-Tyr-D-Val-D-Asp-D-Lys-D-Arg (SEQ ID NO:1),
D-Tyr-D-Val-D-Asp-D-Lys-D-Arg-NH$_2$ (SEQ ID NO:2),
Ac-D-Tyr-D-Val-D-Asp-D-Lys-D-Arg-NH$_2$ (SEQ ID NO:3),
D-Tyr-D-Val-D-Asp-D-Lys-D-Arg-NHMe (SEQ ID NO:4),
Ac-D-Tyr-D-Val-D-Asp-D-Lys-D-Arg-NHMe (SEQ ID NO:5), and
D-Tyr-D-Val-D-Asp-D-Lys-D-Asp-NH$_2$ (SEQ ID NO:7).

Embodiment 8: The method according to Embodiment 5, wherein R is H, $X_1$ is D-Tyr, $X_2$ is D-Val, $X_3$ is D-Asp, $X_4$ is D-Lys, $X_5$ is D-Arg, and R' is OH (SEQ ID NO:1).

Embodiment 9: The method according to Embodiment 5, wherein said polypeptide is administered intrathecally, intravenously, orally, and/or subcutaneously.

Embodiment 10: The method according to Embodiment 5, wherein said polypeptide is administered in an amount ranging from 0.1 mg/kg of said subject to 50 mg/kg of said subject.

Embodiment 11: The method according to Embodiment 5, wherein said polypeptide is administered in an amount ranging from 0.1 mg/kg of said subject to 10 mg/kg of said subject.

Embodiment 12: The method according to Embodiment 5, wherein said polypeptide is administered in an amount ranging from 0.1 mg/kg of said subject to 1 mg/kg of said subject.

Embodiment 13: The method according to Embodiment 5, wherein said polypeptide is lyophilized and reconstituted with an appropriate amount of diluent selected from the group consisting of distilled water and/or sodium chloride.

Embodiment 15: The method according to Embodiment 14, wherein said inflammatory disorder is selected from the group consisting of ankylosing spondylitis, chronic renal disease, Crohn's disease, dysregulated inflammatory response, hidradenitis suppurativa, inflammation, juvenile idiopathic arthritis, non-radiographic axial spondyloarthritis, non-infectious uveitis, neuroinflammation, plaque psoriasis, psoriasis, psoriatic arthritis, renal disease, rheumatoid arthritis, and ulcerative colitis.

Embodiment 16: The method according to Embodiment 14, wherein said $X_1$-$X_2$-$X_3$-$X_4$-$X_5$ is selected from the group consisting of:
D-Tyr-D-Val-D-Asp-D-Lys-D-Arg (SEQ ID NO:1),
D-Tyr-D-Val-D-Asp-D-Lys-D-Arg-NH$_2$ (SEQ ID NO:2),
Ac-D-Tyr-D-Val-D-Asp-D-Lys-D-Arg-NH$_2$ (SEQ ID NO:3),
D-Tyr-D-Val-D-Asp-D-Lys-D-Arg-NHMe (SEQ ID NO:4),
Ac-D-Tyr-D-Val-D-Asp-D-Lys-D-Arg-NHMe (SEQ ID NO:5), and
D-Tyr-D-Val-D-Asp-D-Lys-D-Asp-NH$_2$ (SEQ ID NO:7).

Embodiment 17: The method according to Embodiment 14, wherein R is H, $X_1$ is D-Tyr, $X_2$ is D-Val, $X_3$ is D-Asp, $X_4$ is D-Lys, $X_5$ is D-Arg, and R' is OH (SEQ ID NO:1).

Embodiment 18: The method according to Embodiment 14, wherein said polypeptide is administered intrathecally, intravenously, orally, and/or subcutaneously.

Embodiment 19: The method according to Embodiment 14, wherein said polypeptide is administered in an amount ranging from 0.1 mg/kg of said subject to 50 mg/kg of said subject.

Embodiment 20: The method according to Embodiment 14, wherein said polypeptide is administered in an amount ranging from 0.1 mg/kg of said subject to 10 mg/kg of said subject.

Embodiment 21: The method according to Embodiment 14, wherein said polypeptide is administered in an amount ranging from 0.1 mg/kg of said subject to 1 mg/kg of said subject.

Embodiment 22: The method according to Embodiment 14, wherein said polypeptide is lyophilized and reconstituted with an appropriate amount of diluent selected from the group consisting of distilled water and/or sodium chloride.

---

SEQUENCE LISTING

```
Sequence total quantity: 11
SEQ ID NO: 1            moltype = AA  length = 5
FEATURE                 Location/Qualifiers
source                  1..5
                        mol_type = protein
                        organism = synthetic construct
SITE                    1
                        note = D- Tyrosine
SITE                    2
                        note = D-Valine
SITE                    3
                        note = D- Aspartic Acid
SITE                    4
                        note = D- Lysine
SITE                    5
                        note = D- Arginine
SEQUENCE: 1
YVDKR                                                                    5

SEQ ID NO: 2            moltype = AA  length = 5
FEATURE                 Location/Qualifiers
source                  1..5
                        mol_type = protein
                        organism = synthetic construct
SITE                    1
                        note = D- Tyrosine
SITE                    2
                        note = D-Valine
SITE                    3
                        note = D- Aspartic Acid
```

-continued

```
SITE             4
                 note = D- Lysine
SITE             5
                 note = D- Arginine
MOD_RES          5
                 note = AMIDATION
SEQUENCE: 2
YVDKR                                                                            5

SEQ ID NO: 3     moltype = AA  length = 5
FEATURE          Location/Qualifiers
source           1..5
                 mol_type = protein
                 organism = synthetic construct
SITE             1
                 note = D- Tyrosine
SITE             2
                 note = D-Valine
SITE             3
                 note = D- Aspartic Acid
SITE             4
                 note = D- Lysine
SITE             5
                 note = D- Arginine
MOD_RES          5
                 note = AMIDATION
MOD_RES          1
                 note = ACETYLATION
SEQUENCE: 3
YVDKR                                                                            5

SEQ ID NO: 4     moltype = AA  length = 5
FEATURE          Location/Qualifiers
source           1..5
                 mol_type = protein
                 organism = synthetic construct
SITE             1
                 note = D- Tyrosine
SITE             2
                 note = D-Valine
SITE             3
                 note = D- Aspartic Acid
SITE             4
                 note = D- Lysine
SITE             5
                 note = D- Arginine
MOD_RES          5
                 note = AMIDATION
MOD_RES          5
                 note = METHYLATION
SEQUENCE: 4
YVDKR                                                                            5

SEQ ID NO: 5     moltype = AA  length = 5
FEATURE          Location/Qualifiers
source           1..5
                 mol_type = protein
                 organism = synthetic construct
SITE             1
                 note = D- Tyrosine
SITE             2
                 note = D-Valine
SITE             3
                 note = D-Aspartic Acid
SITE             4
                 note = D-Lysine
SITE             5
                 note = D-Arginine
MOD_RES          1
                 note = ACETYLATION
MOD_RES          5
                 note = AMIDATION
MOD_RES          5
                 note = METHYLATION
SEQUENCE: 5
YVDKR                                                                            5
```

| | | |
|---|---|---|
| SEQ ID NO: 6 | moltype = AA  length = 5 | |
| FEATURE | Location/Qualifiers | |
| source | 1..5 | |
| | mol_type = protein | |
| | organism = synthetic construct | |
| SEQUENCE: 6 | | |
| RKDVY | | 5 |
| | | |
| SEQ ID NO: 7 | moltype = AA  length = 5 | |
| FEATURE | Location/Qualifiers | |
| source | 1..5 | |
| | mol_type = protein | |
| | organism = synthetic construct | |
| SITE | 1 | |
| | note = D-Tyrosine | |
| SITE | 2 | |
| | note = D-Valine | |
| SITE | 3 | |
| | note = D-Aspartic Acid | |
| SITE | 4 | |
| | note = D-Lysine | |
| SITE | 5 | |
| | note = D-Aspartic Acid | |
| MOD_RES | 5 | |
| | note = AMIDATION | |
| SEQUENCE: 7 | | |
| YVDKD | | 5 |
| | | |
| SEQ ID NO: 8 | moltype = AA  length = 5 | |
| FEATURE | Location/Qualifiers | |
| source | 1..5 | |
| | mol_type = protein | |
| | organism = synthetic construct | |
| MOD_RES | 5 | |
| | note = AMIDATION | |
| SEQUENCE: 8 | | |
| RKDVY | | 5 |
| | | |
| SEQ ID NO: 9 | moltype = AA  length = 5 | |
| FEATURE | Location/Qualifiers | |
| source | 1..5 | |
| | mol_type = protein | |
| | organism = synthetic construct | |
| MOD_RES | 1 | |
| | note = ACETYLATION | |
| MOD_RES | 5 | |
| | note = AMIDATION | |
| SEQUENCE: 9 | | |
| RKDVY | | 5 |
| | | |
| SEQ ID NO: 10 | moltype = AA  length = 5 | |
| FEATURE | Location/Qualifiers | |
| source | 1..5 | |
| | mol_type = protein | |
| | organism = synthetic construct | |
| MOD_RES | 5 | |
| | note = AMIDATION | |
| MOD_RES | 5 | |
| | note = METHYLATION | |
| SEQUENCE: 10 | | |
| RKDVY | | 5 |
| | | |
| SEQ ID NO: 11 | moltype = AA  length = 5 | |
| FEATURE | Location/Qualifiers | |
| source | 1..5 | |
| | mol_type = protein | |
| | organism = synthetic construct | |
| MOD_RES | 1 | |
| | note = ACETYLATION | |
| MOD_RES | 5 | |
| | note = AMIDATION | |
| MOD_RES | 5 | |
| | note = METHYLATION | |
| SEQUENCE: 11 | | |
| RKDVY | | 5 |

What is claimed is:

1. A method for ameliorating amyotrophic lateral sclerosis (ALS) in a subject suffering from ALS comprising administering to said subject an effective amount of a polypeptide selected from the group consisting of:
   a polypeptide comprising amino acid sequence D-Tyr-D-Val-D-Asp-D-Lys-D-Arg (SEQ ID NO:1),
   a polypeptide comprising amino acid sequence D-Tyr-D-Val-D-Asp-D-Lys-D-Arg-NH$_2$ (SEQ ID NO:2),
   a polypeptide comprising amino acid sequence Ac-D-Tyr-D-Val-D-Asp-D-Lys-D-Arg-NH$_2$ (SEQ ID NO:3),
   a polypeptide comprising amino acid sequence D-Tyr-D-Val-D-Asp-D-Lys-D-Arg-NHMe (SEQ ID NO:4),
   a polypeptide comprising amino acid sequence Ac-D-Tyr-D-Val-D-Asp-D-Lys-D-Arg-NHMe (SEQ ID NO:5), and
   a polypeptide comprising amino acid sequence D-Tyr-D-Val-D-Asp-D-Lys-D-Asp-NH$_2$ (SEQ ID NO:7).

2. The method according to claim 1, wherein the polypeptide consists of an amino acid sequence set forth in SEQ ID NO: 1.

3. The method according to claim 1, wherein said polypeptide is administered intrathecally, intravenously, orally, and/or subcutaneously.

4. The method according to claim 1, wherein said polypeptide is administered in an amount ranging from 1 mg/kg of said subject to 50 mg/kg of said subject.

5. The method according to claim 1, wherein said polypeptide is administered in an amount ranging from 1 mg/kg of said subject to 10 mg/kg of said subject.

6. The method according to claim 1, wherein said polypeptide is administered in an amount ranging from 1 mg/kg of said subject to 1 mg/kg of said subject.

7. The method according to claim 1, wherein said polypeptide is lyophilized and reconstituted with an appropriate amount of diluent selected from the group consisting of distilled water and/or sodium chloride.

8. The method according to claim 2, wherein said polypeptide is administered in an amount of 0.04 mg/kg of said subject given every 48 hours.

9. The method according to claim 2, wherein said polypeptide is administered in a total amount of 2 mg/kg of said subject every other day.

10. The method according to claim 2, wherein said polypeptide is administered subcutaneously in an amount of 0.04 mg/kg of said subject given every 48 hours.

11. The method according to claim 1, wherein the polypeptide consists of the amino acid
   D-Tyr-D-Val-D-Asp-D-Lys-D-Arg (SEQ ID NO:1),
   D-Tyr-D-Val-D-Asp-D-Lys-D-Arg-NH$_2$ (SEQ ID NO:2),
   Ac-D-Tyr-D-Val-D-Asp-D-Lys-D-Arg-NH$_2$ (SEQ ID NO:3),
   D-Tyr-D-Val-D-Asp-D-Lys-D-Arg-NHMe (SEQ ID NO:4),
   Ac-D-Tyr-D-Val-D-Asp-D-Lys-D-Arg-NHMe (SEQ ID NO:5), or
   D-Tyr-D-Val-D-Asp-D-Lys-D-Asp-NH$_2$ (SEQ ID NO:7).

12. A method for ameliorating chronic renal disease, renal disease, and/or end-stage renal disease in a subject suffering therefrom comprising administering to said subject an effective amount of a polypeptide selected from the group consisting of:
   a polypeptide comprising amino acid sequence D-Tyr-D-Val-D-Asp-D-Lys-D-Arg (SEQ ID NO:1),
   a polypeptide comprising amino acid sequence D-Tyr-D-Val-D-Asp-D-Lys-D-Arg-NH$_2$ (SEQ ID NO:2),
   a polypeptide comprising amino acid sequence Ac-D-Tyr-D-Val-D-Asp-D-Lys-D-Arg-NH$_2$ (SEQ ID NO:3),
   a polypeptide comprising amino acid sequence D-Tyr-D-Val-D-Asp-D-Lys-D-Arg-NHMe (SEQ ID NO:4),
   a polypeptide comprising amino acid sequence Ac-D-Tyr-D-Val-D-Asp-D-Lys-D-Arg-NHMe (SEQ ID NO:5), and
   a polypeptide comprising amino acid sequence D-Tyr-D-Val-D-Asp-D-Lys-D-Asp-NH$_2$ (SEQ ID NO:7).

13. The method according to claim 12, wherein the polypeptide consists of an amino acid sequence set forth in SEQ ID NO: 1.

14. The method according to claim 12, wherein said polypeptide is administered intrathecally, intravenously, orally, and/or subcutaneously.

15. The method according to claim 12, wherein said polypeptide is administered in an amount ranging from 1 mg/kg of said subject to 50 mg/kg of said subject.

16. The method according to claim 12, wherein said polypeptide is administered in an amount ranging from 1 mg/kg of said subject to 10 mg/kg of said subject.

17. The method according to claim 12, wherein said polypeptide is administered in an amount ranging from 1 mg/kg of said subject to 1 mg/kg of said subject.

18. The method according to claim 12, wherein said polypeptide is lyophilized and reconstituted with an appropriate amount of diluent selected from the group consisting of distilled water and/or sodium chloride.

19. The method according to claim 13, wherein said polypeptide is administered in an amount of 0.04 mg/kg of said subject given every 48 hours.

20. The method according to claim 13, wherein said polypeptide is administered in a total amount of 2 mg/kg of said subject every other day.

21. The method according to claim 13, wherein said polypeptide is administered subcutaneously in an amount of 0.04 mg/kg of said subject given every 48 hours.

22. The method according to claim 12, wherein the polypeptide consists of the amino acid sequence
   D-Tyr-D-Val-D-Asp-D-Lys-D-Arg (SEQ ID NO:1),
   D-Tyr-D-Val-D-Asp-D-Lys-D-Arg-NH$_2$ (SEQ ID NO:2),
   Ac-D-Tyr-D-Val-D-Asp-D-Lys-D-Arg-NH$_2$ (SEQ ID NO:3),
   D-Tyr-D-Val-D-Asp-D-Lys-D-Arg-NHMe (SEQ ID NO:4),
   Ac-D-Tyr-D-Val-D-Asp-D-Lys-D-Arg-NHMe (SEQ ID NO:5), or
   D-Tyr-D-Val-D-Asp-D-Lys-D-Asp-NH$_2$ (SEQ ID NO:7).

* * * * *